(12) United States Patent
Shu et al.

(10) Patent No.: US 10,702,370 B2
(45) Date of Patent: *Jul. 7, 2020

(54) LUMEN STENT

(71) Applicant: LIFETECH SCIENTIFIC (SHENZHEN) CO., LTD, Shenzhen (CN)

(72) Inventors: Chang Shu, Shenzhen (CN); Benhao Xiao, Shenzhen (CN); Deyuan Zhang, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 35 days.

This patent is subject to a terminal disclaimer.

(21) Appl. No.: 16/067,323

(22) PCT Filed: Dec. 23, 2016

(86) PCT No.: PCT/CN2016/111700
§ 371 (c)(1),
(2) Date: Jun. 29, 2018

(87) PCT Pub. No.: WO2017/114305
PCT Pub. Date: Jul. 6, 2017

(65) Prior Publication Data
US 2019/0000606 A1    Jan. 3, 2019

(30) Foreign Application Priority Data
Dec. 30, 2015 (CN) .......................... 2015 1 1019845

(51) Int. Cl.
*A61F 2/07* (2013.01)
*A61F 2/97* (2013.01)
(Continued)

(52) U.S. Cl.
CPC ................. *A61F 2/07* (2013.01); *A61F 2/97* (2013.01); *A61F 2/848* (2013.01); *A61F 2/852* (2013.01);
(Continued)

(58) Field of Classification Search
CPC ........ A61F 2/06; A61F 2/07; A61F 2002/072; A61F 2/852
See application file for complete search history.

(56) References Cited

U.S. PATENT DOCUMENTS 6,015,431 A    1/2000 Thornton et al.
2009/0105805 A1    4/2009 Baker et al.
(Continued)

FOREIGN PATENT DOCUMENTS

CN    201701341 U    1/2011
CN    203576697 U    5/2014
(Continued)

OTHER PUBLICATIONS

International Search Report dated Mar. 27, 2017 of corresponding International Application No. PCT/CN2016/111700; 9 pgs.
(Continued)

*Primary Examiner* — Jason-Dennis N Stewart
(74) *Attorney, Agent, or Firm* — Maier & Maier, PLLC

(57) ABSTRACT

A lumen stent includes a first tube body and a second tube body. The second body is sleeved outside the first body and has at least one end in hermetic connection with the outer surface of the first body. The second body includes a thin film body that covers at least part of the first body and a second radial supporting structure that is disposed in a maximum radius-length region of the thin film body and surrounds the maximum radius-length region. The second radial supporting structure has radius supporting property. After the implantation of the lumen stent, a semi-enclosed
(Continued)

gap can be formed between the first body and the second body, or a semi-enclosed gap can be formed between the second body and a tube wall, so that blood flowing into the gap can serve as a filling material and prevent blood from flowing into a tumor body.

13 Claims, 11 Drawing Sheets

(51) Int. Cl.
*A61F 2/848* (2013.01)
*A61F 2/06* (2013.01)
*A61F 2/852* (2013.01)
*A61F 2/89* (2013.01)

(52) U.S. Cl.
CPC ........... *A61F 2/89* (2013.01); *A61F 2002/061* (2013.01); *A61F 2002/065* (2013.01); *A61F 2002/077* (2013.01); *A61F 2002/8486* (2013.01); *A61F 2210/0076* (2013.01); *A61F 2220/005* (2013.01); *A61F 2220/0058* (2013.01); *A61F 2220/0075* (2013.01); *A61F 2250/0018* (2013.01); *A61F 2250/0039* (2013.01); *A61F 2250/0063* (2013.01); *A61F 2250/0069* (2013.01)

(56) References Cited

U.S. PATENT DOCUMENTS

| | | |
|---|---|---|
| 2013/0297001 A1 | 11/2013 | Kasprzak et al. |
| 2014/0350658 A1* | 11/2014 | Benary ................... A61F 2/07 |
| | | 623/1.15 |
| 2015/0073523 A1 | 3/2015 | Chobotov |
| 2015/0202065 A1 | 7/2015 | Shalev et al. |
| 2016/0067067 A1* | 3/2016 | Roselli ................... A61F 2/07 |
| | | 623/1.16 |

FOREIGN PATENT DOCUMENTS

| | | |
|---|---|---|
| CN | 105496603 A | 4/2016 |
| CN | 105662511 A | 6/2016 |
| CN | 205458864 U | 8/2016 |
| CN | 205494093 U | 8/2016 |

OTHER PUBLICATIONS

First Office Action dated Sep. 11, 2017 of corresponding Chinese Application No. 201511019845.6; 16 pgs.
Search Report dated Sep. 3, 2017 of corresponding Chinese Application No. 201511019845.6; 1 pg.
Second Office Action dated May 8, 2018 of corresponding Chinese Application No. 201511019845.6; 3 pgs.

* cited by examiner

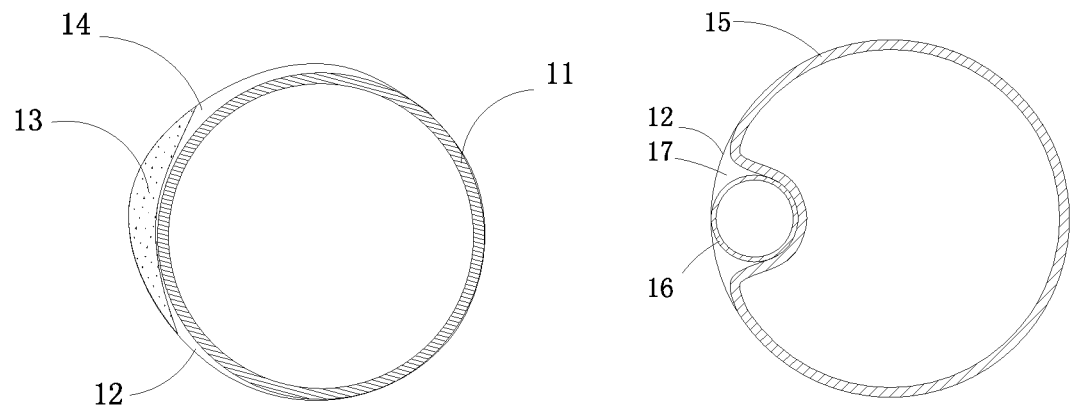
Fig. 1
(Prior Art)
Fig. 2
(Prior Art)
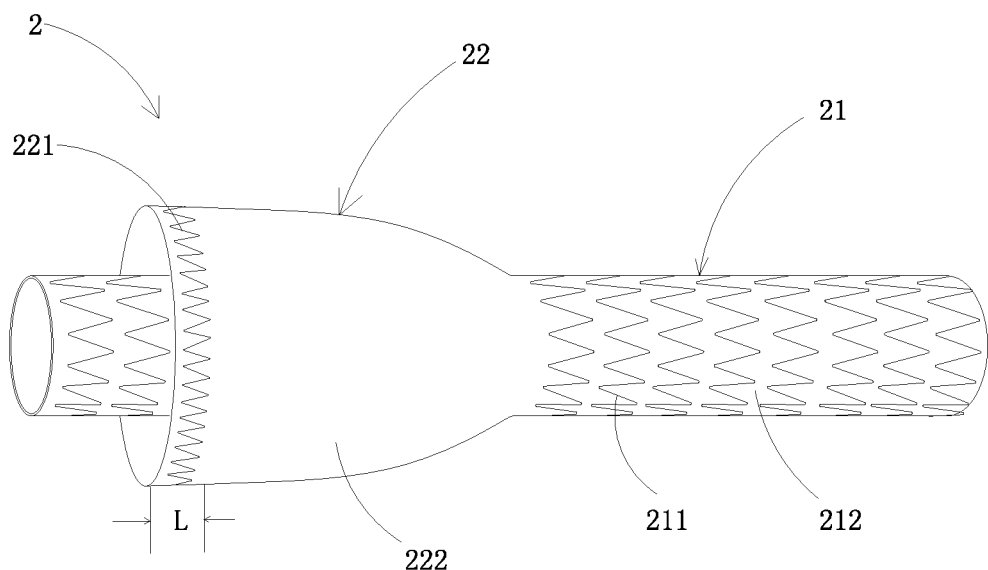
Fig. 3

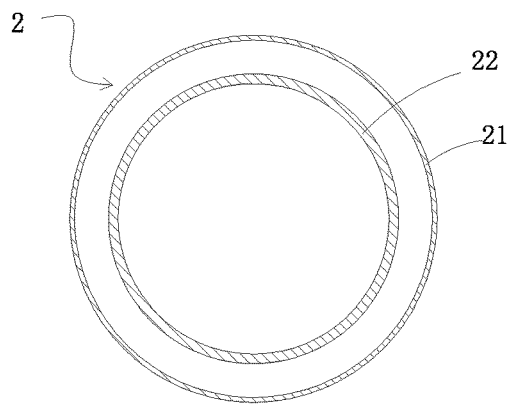
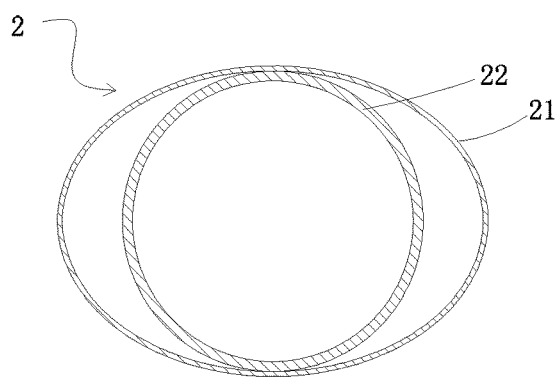
Fig. 9        Fig. 10
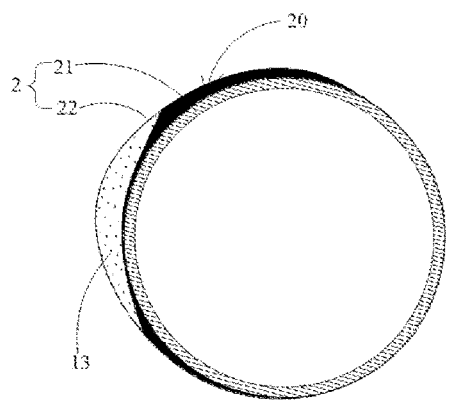
Fig. 11
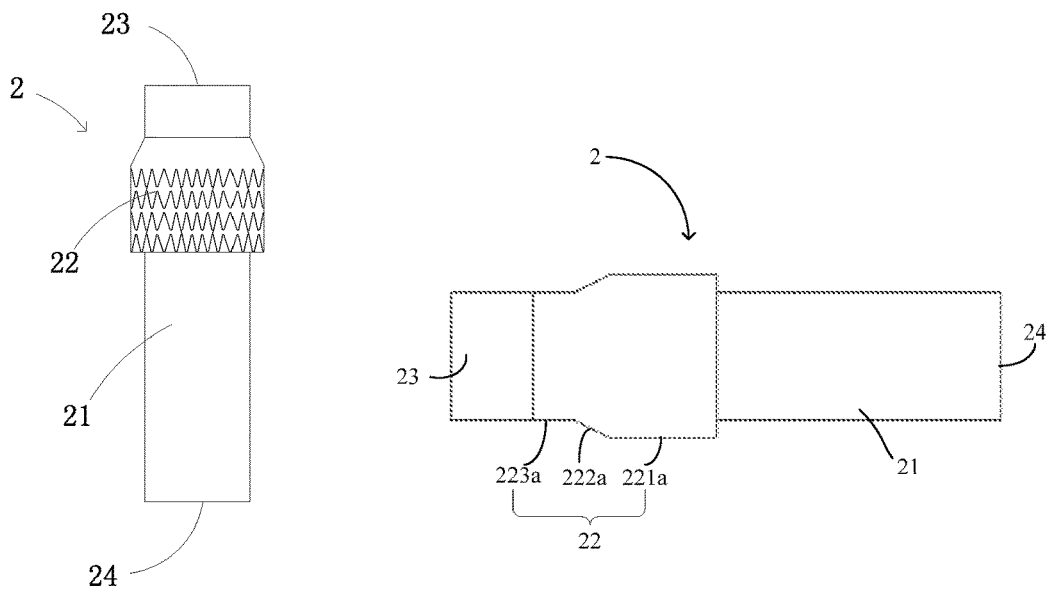
Fig. 12        Fig. 13A

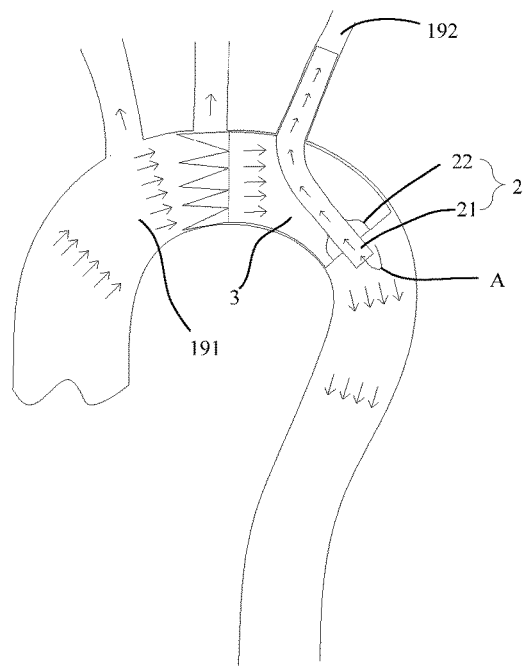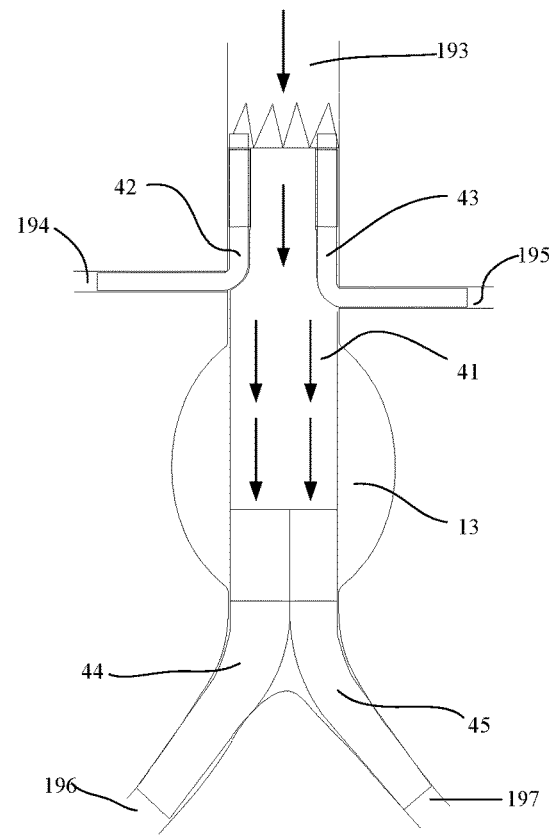
Fig. 21
Fig. 22
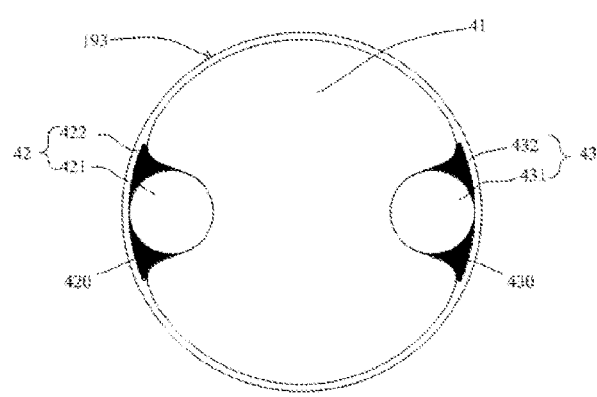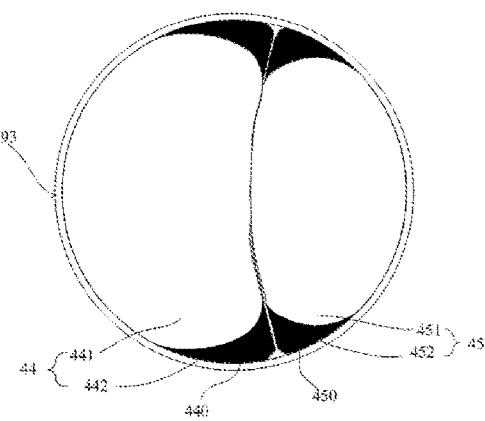
Fig. 23
Fig. 24

LUMEN STENT

FIELD

The present application relates to an implanted medical device, and more particularly relates to a luminal stent graft and a luminal stent graft system.

BACKGROUND

At present, a luminal stent graft may be adopted to implement endovascular graft exclusion to isolate a diseased region in a human body lumen, for example, the luminal stent graft may be adopted to isolate an artery dissection or an arterial aneurysm in a blood vessel. This kind of method has gradually substituted traditional invasive operation due to its advantages of a small operation wound, small intra-operative blood transfusion volume, quick postoperative recovery, short hospital stay, and the like. The luminal stent generally has radial expandability, and is clung to a vascular cavity wall by using its radial supporting force so as to be fixed in a lumen. To prevent the stent graft from falling off, the stent graft needs to have a high enough radial supporting force, but the higher radial supporting force indicates higher rigidity of the radially unfolded stent. However, due to individual differences, the inner walls of lumens are of different shapes, and also may have calcified plaques that would change their shapes; and the luminal stent graft with relatively high rigidity may possibly result in a poor or decreased ability to cling to a luminal wall, so that a space between the stent graft and a diseased luminal wall may not be completely closed.

For example, with reference to FIG. 1, a plaque 13 on the inner wall of a lumen 12 may form a clearance 14 between a stent graft 11 and the inner wall of the lumen 12, and blood flow may flow to a tumor cavity or a dissection false cavity through the clearance 14, thus generating type-I endoleak. Alternatively, to open up main body blood vessels and branch blood vessels at the same time, multiple stent grafts are used cooperatively by adopting a chimney technology, a periscope technology or a sandwich technology, and then are respectively implanted into the main body blood vessels and the branch blood vessels. For example, with reference to FIG. 2, one end of a main body stent graft 15 and one end of a branch stent graft 16 are abreast implanted into the lumen 12, and the other end of the main body stent graft 15 is communicated with a relatively large main body blood vessel (not shown in the figure), but the other end of the branch stent graft 16 is communicated with a relatively small branch blood vessel (not shown in the figure). To make sure that the blood flow flowing into the branch blood vessel is unblocked, the radial supporting force of the branch stent graft 16 needs to be greater than that of the main body stent graft 15, and this would lead to a situation that portions, which are located at the abreast implanted positions, of the main body stent graft 15 are easier to deform radially to form a clearance 17 among the branch stent graft 16, the main body stent graft 15 and the inner wall of the lumen 12, thus generating the type-I endoleak, and the blood flow may flow to the tumor cavity or the dissection false cavity through the clearance 17.

This type-I endoleak may appear in a thoracic aorta, an abdominal aorta or other lumens. Continuous inflow of the blood flow may cause continuous enlargement of the dissection false cavity or an arterial aneurysm cavity, and finally result in a serious consequence of breakage of the dissection false cavity or the arterial aneurysm cavity, so that the endovascular graft exclusion may fail. Therefore, to enhance the surgical effect and increase the healing success rate, it is very important for the luminal stent graft used in the endovascular graft exclusion to avoid the type-I endoleak between the stent graft and the lumen as much as possible.

SUMMARY

To solve the technical problems and overcome the shortcomings in the prior art, the present application provides a luminal stent graft capable of avoiding formation of an endoleak.

The present application adopts a technical scheme shown and described herein to solve the technical problem: a luminal stent graft is provided, including a first tubular body and a second tubular body; the second tubular body is sleeved outside the first tubular body, and at least one end of the second tubular body is sealingly connected with the outer surface of the first tubular body; the second tubular body includes a graft covering at least one portion of the first tubular body and a second radial supporting structure which is arranged in a maximum radial length region of the graft and surrounds the maximum radial length region; and the second radial supporting structure has radial supportability. In the luminal stent graft according to the embodiment of the present application, the first tubular body includes at least one first radial supporting structure distributed along a circumferential direction of the first tubular body.

In the luminal stent graft according to the embodiment of the present application, in a naturally unfolded state, at the same position in a radial supporting section, the radial length of the second radial supporting structure is 1.3 times to 3 times the radial length of the first radial supporting structure.

In the luminal stent graft according to the embodiment of the present application, in the naturally unfolded state, the radial length of the second radial supporting structure is more than that of the first radial supporting structure by 2 mm to 30 mm.

In the luminal stent graft according to the embodiment of the present application, the radial deformability of the second radial supporting structure is greater than that of the first radial supporting structure.

In the luminal stent graft according to the embodiment of the present application, under the action of the same radial force, a radial length variation of the second radial supporting structure is greater than that of the first radial supporting structure; or under the action of the same radial force, a radial length change rate of the second radial supporting structure is greater than that of the first radial supporting structure; or in case of the same radial change rate or the same radial variation, a radial external force exerted on the first radial supporting structure is greater than that exerted on the second radial supporting structure.

In the luminal stent graft according to the embodiment of the present application, the second radial supporting structure is a waveform ring-like object; and in the naturally unfolded state, a maximum width m of any waveform of the waveform ring-like object along a circumferential direction and a perimeter D of the second tubular body at the waveform accord with a condition that m is less than or equal to D/8 or m is less than or equal to D/10 or m is less than or equal to D/12 or m is less than or equal to D/13 or m is less than or equal to D/14.

In the luminal stent graft according to the embodiment of the present application, the second radial supporting structure is of a meshed structure including multiple grids; and in a naturally unfolded state, a maximum width m1 of any grid along the circumferential direction and the perimeter D of the second tubular body at the grid accord with a condition that m1 is less than or equal to D/12 or m1 is less than or equal to D/13 or m1 is less than or equal to D/14.

In the luminal stent graft according to the embodiment of the present application, in the portion covered by a graft, the first tubular body further includes a first graft covering the first radial supporting structure.

In the luminal stent graft according to the embodiment of the present application, one end of the graft is sealingly connected with the first tubular body, and the other end of the graft is open; and the maximum radial length region of the graft is located near to an opening of the open end, or is located at the middle portion of the graft.

In the luminal stent graft according to the embodiment of the present application, two ends of the graft are sealingly connected with the first tubular body, and the maximum radial length region of the graft is located at the middle portion of the graft.

In the luminal stent graft according to the embodiment of the present application, at least one end of the first tubular body has multiple convex pieces extending in parallel to the longitudinal axis of the first tubular body, and a gap is reserved between two adjacent convex pieces.

In the luminal stent graft according to the embodiment of the present application, the first tubular body includes four wave loops arrayed in sequence along a longitudinal central axis direction of the first tubular body, and the four wave loops are connected through square connecting rings.

In the luminal stent graft according to the embodiment of the present application, the first tubular body includes barrel-shaped inner grafts, wave loops and annular outer grafts; the wave loops are arranged between the barrel-shaped inner graft and the annular outer graft in a clamping manner; and at least part of wave crests and/or wave troughs of the wave loops are exposed outside.

In the luminal stent graft according to the embodiment of the present application, a graft is arranged on the first tubular body; and a hole penetrating through the graft is formed in a portion, which is near to the end portion of the first tubular body, on the graft or the wave loop, which is close to the end portion of the first tubular body, of the first tubular body is not completely covered by the graft.

After the luminal stent graft according to the embodiment of the present application is implanted, a semi-closed clearance may be formed between the first tubular body and the second tubular body, or a semi-closed clearance is formed between the second tubular body and a lumen wall; and a blood flowing into the clearance may be used as a filler material to occlude a type-I endoleak channel, thus avoiding the blood from flowing into a tumor body or a dissection.

BRIEF DESCRIPTION OF THE DRAWINGS

A further description will be made to the present application below in conjunction with accompanying drawings and embodiments. In these drawings:

FIG. 1 is a schematic diagram of a single luminal stent graft implanted into a lumen having a plaque in the prior art;

FIG. 2 is a schematic diagram of two luminal stent grafts implanted into a lumen cooperatively in the prior art;

FIG. 3 is a schematic diagram of a structure of an example luminal stent graft according to a first embodiment of the present application;

FIG. 9 is a radial section diagram of a luminal stent graft in a naturally unfolded state according to the second embodiment of the present application;

FIG. 10 is a radial section diagram of the radially compressed luminal stent graft in FIG. 9;

FIG. 11 is a schematic diagram of a single luminal stent graft implanted into a lumen having a plaque according to the second embodiment of the present application;

FIG. 12 is a schematic diagram of a luminal stent graft according to a third embodiment of the present application;

FIG. 13A is a schematic diagram of a specific structure of the luminal stent graft of FIG. 12;

FIG. 21 is a schematic diagram of another example structure of a luminal stent graft system according to the sixth embodiment of the present application;

FIG. 22 is a schematic diagram of a luminal stent graft system according to a seventh embodiment of the present application;

FIG. 23 is a radial section diagram of a portion near to the renal artery after the luminal stent graft system in FIG. 22 is implanted;

FIG. 24 is a radial section diagram of a portion near to the ilium artery after the luminal stent graft system in FIG. 22 is implanted;

DETAILED DESCRIPTION

Figure 4:
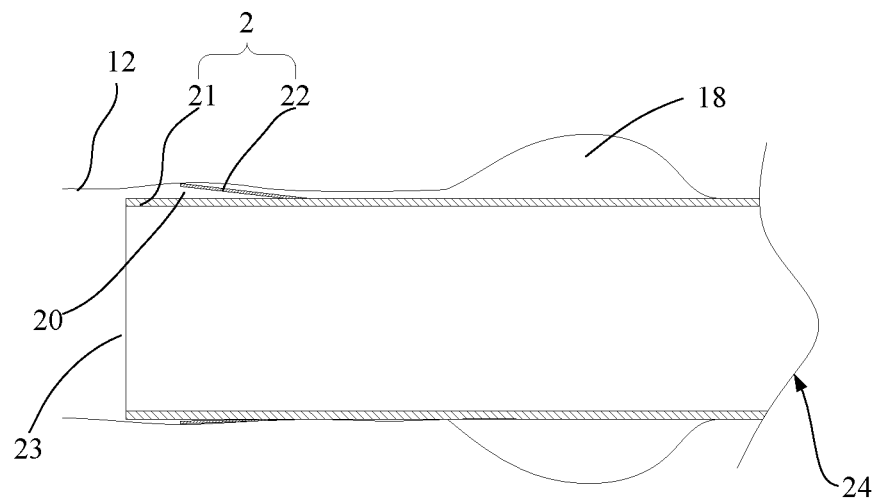
FIG. 4 is an axial section diagram of a single luminal stent graft implanted into a lumen according to the first embodiment of the present application.

For the purpose of making technical features, objectives and effects of the present application clearer, now a detailed description will be made to specific implementation modes of the present application with reference to the drawings.

First Embodiment

With reference to FIG. 3, a luminal stent graft 2 according to the first embodiment of the present application includes a first tubular body 21 and a second tubular body 22; the second tubular body 22 is sleeved outside the first tubular body 21, and covers at least one portion of the first tubular body 21; and one end of the second tubular body 22 is sealingly connected with the peripheral surface of the first tubular body 21.

In this embodiment, the first tubular body 21 has radial expandability, may be compressed under the action of an external force, and restores an initial shape through self-expansion or mechanical expansion (such as balloon dilatation expansion) and keeps the initial shape after the external force is withdrawn, so that after being implanted into a lumen, the first tubular body 21 may cling to the lumen wall through its radial supporting force to be fixed in the lumen. The first tubular body 21 includes a first radial supporting structure 211 arranged on the whole tubular body, for example, the first radial supporting structure 211 may be made of a memory alloy material (for example a nickel-titanium alloy), thereby having self-expansion capacity. The first radial supporting structure 211 may include multiple turns of waveform ring-like objects distributed along an axial direction, or may be of a meshed structure formed by weaving a metal wire, or may be of a cut meshed structure formed by cutting a metal tube. A person of ordinary skill in the art can select a proper first radial supporting structure 211 according to a desire or requirement, so, for the sake of brevity, no further details are described herein. In addition, at least a region, which is not covered by the second tubular body 22, of the first tubular body 21 also includes a first graft 212; and the first graft 212 may be a PET (polyethylene terephthalate) film or a PTFE (polytetrafluoroethylene) film, and may cover the first radial supporting structure 211 in a suturing or hot melting way.

The second tubular body 22 has radial expandability. Namely it may be compressed under the action of an external force, restores to an initial shape through self-expansion or mechanical expansion (such as balloon dilatation expansion), and keeps the initial shape after the external force is withdrawn, so that after being implanted into the lumen, the second tubular body 22 may cling to the lumen wall through its radial supporting force. The second tubular body 22 includes a graft 222 and a second radial supporting structure 221 which is arranged in a maximum radial length region L of the graft 222 and surrounds the maximum radial length region L; and the second tubular body 22 has the above-mentioned radial expandability, or radial supportability or radial supporting force, due to its second radial supporting structure 221. For example, the second radial supporting structure 221 may be made of a memory alloy material (for example a nickel-titanium alloy), thereby having self-expansion capacity. The second radial supporting structure 221 may include multiple turns of waveform ring-like objects distributed along an axial direction, or may be a mesh structure formed by weaving metal wire, or may be of a cut mesh structure formed by cutting a metal tube. A person of ordinary skill in the art can select a proper second radial supporting structure 221 according to a desire or requirement, so, for the sake of brevity, no further details are described herein. The graft 222 may be a PET film or a PTFE film, and may cover the second radial supporting structure 221 in a suturing or hot melting manner. It can be understood that under the same condition, the radial supporting force of the second radial supporting structure is greater than that of the graft.

One end of the second tubular body 22 and the first tubular body 21 may be sealingly connected via hot melting of the graft 222 and the first graft 212, and also may be sealingly connected by suturing the graft 222 onto the first graft 212. A person of ordinary skill in the art can select a proper sealing way according to a desire or requirement, so, for the sake of brevity, no further details are described herein.

In the example of a luminal stent graft, as shown in FIG. 3, one end of the graft 222 is sealingly connected with the first tubular body 21, and the other end of the graft 222 is open; and the maximum radial length region L of the graft 222 is located near to an opening of the open end, and of course, the maximum radial length region L may be located at the middle portion of the graft 222.

With reference to FIG. 4, one end of the second tubular body 22 is an open tube orifice; as the second radial supporting structure 221 has the radial supporting force or radial supportability, and is arranged in the maximum radial length region of the graft 222, the second tubular body 22 (namely the graft 222) may be attached to the inner wall of a lumen 12 after being implanted, and an effective clearance 20 is formed between the second tubular body 22 and the first tubular body 21; when flowing into the luminal stent graft 2 from the proximal end 23, a blood also flows into the clearance 20 at the same time; and as the tube orifice in the other end of the second tubular body 22 is closed, the blood flowing into the clearance 20 may achieve a sealing and filling effect, thereby reducing and even avoiding blood flow which flows into the clearance formed between the second tubular body 22 and the inner wall of the lumen and cutting off a channel or an opening that may form type-I endoleak, and this part of blood will be directly thrombosed in the clearance 20 to make the sealing and filling effect better. In the sealing process, no other sealing or filling materials need to be added into the luminal stent graft 2 in advance or after the luminal stent graft 2 is implanted, but sealing also may be realized only through inflowing blood from normal blood circulation, so that no extra biological risk caused by the sealing or filling materials will be increased.

In the specific structure of the luminal stent graft 2, in a naturally unfolded state, at the same position (namely the same radial section) of the maximum radial length region L of the graft 222, the radial length of the second radial supporting structure 221 is 1.3 times to 3 times the radial length of the first radial supporting structure 211, so that at this position, a clearance space is formed between the first tubular body 21 and the second tubular body 22.

Alternatively, at the same position of the maximum radial length region L of the graft 222, the radial length of the second radial supporting structure 221 is more than that of the first radial supporting structure 211 by 2 mm to 30 mm, so that at this position, a clearance space is formed between the first tubular body 21 and the second tubular body 22. In one embodiment, when the radial length of the first tubular body 21 is 20 mm to 48 mm, a corresponding luminal stent graft is generally applied to aorta positions including an ascending aorta, an aorta arch, a thoracic descending aorta and an abdominal aorta; at the moment, the radial length of the second radial supporting structure 221 at the same position is more than that of the first radial supporting structure 211 by 2 mm to 20 mm; when the radial length of the first tubular body 21 is 4 mm to 20 mm, a corresponding luminal stent graft is generally applied to a branch blood vessel such as an arch branch, a renal artery and an iliac artery; at the moment, the radial length of the second radial supporting structure 221 at the same position is more than that of the first radial supporting structure 211 by 3 mm to 30 mm.

As the second tubular body has the radial expandability. Namely it may be compressed under the action of an external force, restores to the initial shape through self-expansion or mechanical expansion (such as balloon dilatation expansion), and keeps the initial shape after the external force is withdrawn, a radial length difference between the first tubular body and the second tubular body or a radial length ratio of the first tubular body to the second tubular body may be valued within a relatively large range. If the radial length difference between the first tubular body and the second tubular body or the radial length ratio of the first tubular body to the second tubular body needs to be relatively small, for example, if the radial length difference is up to 2 mm, 3 mm or 4 mm, the first tubular body and the second tubular body may not be attached together due to their radial expandability, so that the clearance space still exists, and may be kept unblocked; and if the radial length difference between the first tubular body and the second tubular body or the radial length ratio of the first tubular body to the second tubular body needs to be relatively large, for example, if the radial length difference is more than 10 mm, the second tubular body still may effectively cling to the lumen wall, and may not turn over under impact of the blood flow. Therefore, the luminal stent graft according to the embodiment of the present application is wide in application range and high in stability of blocking the leak.

Figure 5:
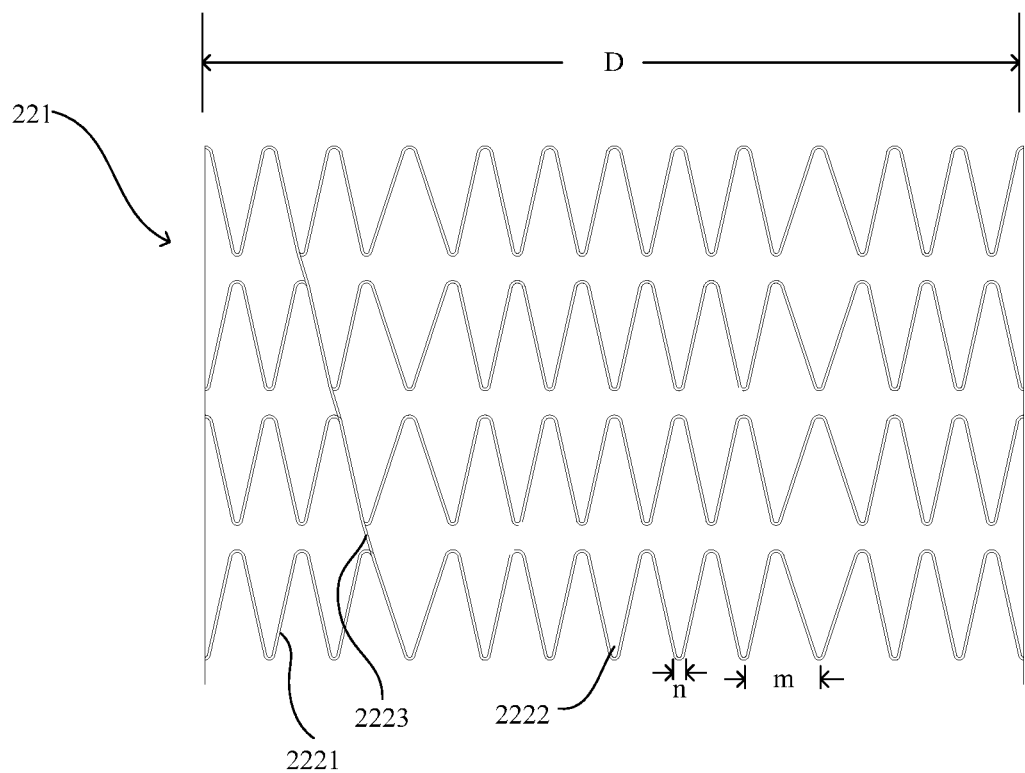
FIG. 5 is a schematic diagram of multiple turns of waveform ring-like objects of one example of a second tubular body in the first embodiment.

In one mode of the second radial supporting structure 221, with reference to FIG. 5, the second radial supporting structure 221 includes at least one turn of waveform ring-like object 2221, and the figure shows four turns of waveform ring-like objects 2221, but this is only used as an example, and is not intended to limit the present application. A person of ordinary skill in the art can select a proper number of waveform ring-like objects 2221 according to a requirement. The waveform ring-like objects 2221 may be formed by winding a metal wire, for example, they may be formed by winding a memory alloy (including a nickel-titanium alloy) wire into a preset waveform; a metal wire with a wire diameter (namely the diameter) of 0.05 mm to 0.4 mm may be selected; and the waveform may be a Z-shaped wave, a U-shaped wave or a sine wave and the like. Or, the waveform ring-like objects also may be formed by cutting a metal tube, and the wire diameter of a metal rod forming the waveform ring-like objects is 0.05 mm to 0.4 mm. This figure shows a schematic diagram of the second radial supporting structure 221 which is unfolded axially, so that the axially unfolded width D here is the perimeter of a portion, which is at the second radial supporting structure 221, of the second tubular body 22.

In addition, by the adoption of the metal wire with the same wire diameter, if the radial length of the second radial supporting structure 221 is larger, the equivalent wire diameter of the second radial supporting structure 221 is smaller, and vice versa. It can be seen from here that an effect of reducing the wire diameter may be achieved by increasing the radial length of the second radial supporting structure 221. Under a circumstance that other conditions are the same, if the equivalent wire diameter of a radial supporting structure is smaller, the radial deformability of the radial supporting structure is higher.

For example, in one implementation mode, if the first radial supporting structure and the second radial supporting structure have same waveform structures and are formed by metal wires having the same wire diameters, the second radial supporting structure has the equivalent wire diameter less than that of the first radial supporting structure due to its relatively large radial length, so that the radial deformability of the second radial supporting structure is greater than that of the first radial supporting structure.

In one embodiment, when the radial length of the second radial supporting structure 221 is 4 mm to 20 mm, the wire diameter of a formed waveform is 0.05 mm to 0.32 mm; when the radial length of the second radial supporting structure 221 is 20 mm to 50 mm, the wire diameter of a wound waveform is 0.1 mm to 0.35 mm; and when the radial length of the second radial supporting structure 221 is 50 mm to 80 mm, the wire diameter of a wound waveform is 0.2 mm to 0.4 mm. The metal wire within the above-mentioned wire diameter range has relatively high bending flexibility, so that a waveform ring-like object formed by winding the metal wire has relatively high radial deformability.

Any turn of waveform ring-like object 2221 includes multiple waveforms, and adjacent waveforms are connected to each other. Any waveform includes two interconnected supporting pieces which are adjacent to each other and form a certain included angle, and a maximum width m of the waveform along the circumferential direction and a perimeter D, which corresponds to the waveform ring-like object with the waveform, of the second tubular body 22 accord with a condition that m is less than or equal to D/12, and m ranges from 1.5 mm to 8 mm. In one embodiment, m may be equal to the maximum relative circumferential distance between two adjacent supporting pieces.

It can be seen from the above that in one circumferential radial supporting structure, for example, in one turn of circumferentially distributed waveform ring-like object, the maximum circumferential distance between two adjacent supporting pieces accords with a condition that m is less than or equal to D/12, for example, also may accord with a condition that m is less than or equal to D/8, or m is less than or equal to D/10, or m is less than or equal to D/13, or m is less than or equal to D/14. Although the maximum circumferential distance (namely the maximum width of the waveform along the circumferential direction) may not provide enough radial supporting force to fix the radial supporting structure in the lumen, the provided radial supporting force is high enough to enable the radial supporting structure to be attached to the lumen wall; and as the maximum circumferential distance is relatively small, the radial supporting structure may be embedded into a tiny or small gap to be attached to the inner walls of lumens in various shapes and avoid the formation of the endoleak. The radial supporting force for fixing the luminal stent graft in the lumen may be provided by the first radial supporting structure in the first tubular body.

To further improve the deformability of the second radial supporting structure complying with the inner wall of the lumen, the waveform height of each of the above-mentioned waveform ring-like objects may be set to be 2 mm to 8 mm. To be specific, when the radial length of the second radial supporting structure 221 is 4 mm to 20 mm, the waveform height is 2 mm to 6 mm; when the radial length of the second radial supporting structure 221 is 20 mm to 50 mm, the wire diameter of a wound waveform is 3 mm to 7 mm; and when the radial length of the second radial supporting structure 221 is 50 mm to 80 mm, the wire diameter of a wound waveform is 4 mm to 8 mm. If the waveform height is smaller, the capacity of complying with the shape deformation of the inner wall of the lumen is higher.

At least one waveform of each waveform ring-like object 2221 has an internal fillet 2222, a maximum width n of the internal fillet 2222 along the circumferential direction accords with a condition that n is less than or equal to 1.5 mm. If the value of n is smaller, the deformability of the second tubular body 22 for complying with the inner wall of the lumen is higher, and the clearance filling capacity is higher, so that the capacity for blocking the endoleak is higher.

Figure 6:
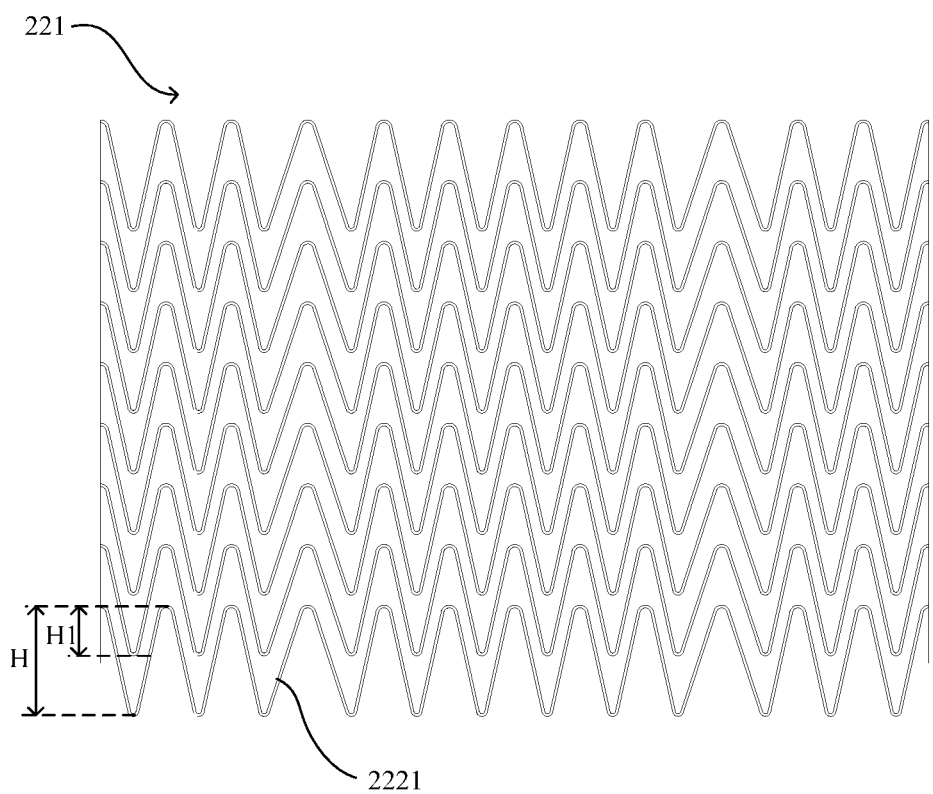
FIG. 6 is a schematic diagram of multiple turns of waveform ring-like objects of a second tubular body in another specific implementation mode.

The second radial supporting structure 221 may include multiple turns of waveform ring-like objects 2221 distributed along an axial direction. There are many ways of distributing the multiple turns of waveform ring-like objects 2221. For example, with reference to FIG. 5, the second radial supporting structure 221 includes at least two adjacent turns of waveform ring-like objects 2221 which are isolated mutually and have no overlapped regions. Namely an axial distance is reserved between any wave crest of one turn of waveform ring-like object and any wave trough of the other adjacent turn of waveform ring-like object, wherein the minimum axial distance may be less than 3 mm. To avoid shortening of the second tubular body 22, connecting rods 2223 also may be arranged to connect the multiple waveform ring-like objects 2221. For another example, with reference to FIG. 6, the second radial supporting structure 221 at least includes two adjacent turns of waveform ring-like objects 2221, wherein the waveforms of one turn of waveform ring-like object are embedded into the waveforms of the other adjacent turn of waveform ring-like object. Namely, an axial distance between any wave crest of one turn of a waveform ring-like object and one of the closest wave crests of the other adjacent turn of the waveform ring-like object is less than the waveform height of this turn of waveform ring-like object. The waveform ring-like objects 2221 in the figure are taken as an example, and one waveform ring-like object is embedded into the other axially adjacent waveform ring-like object according to an embedding depth H1 which accords with a condition that H1 is less than or equal to H/3, where H is the waveform height (namely the axial distance between one wave crest and one wave trough) of the embedded waveform ring-like object 2221.

Second Embodiment

On the basis of the first embodiment, according to a luminal stent graft of the second embodiment, further in the maximum radial length region L of the graft 222, the radial deformability of the second radial supporting structure 221 is greater than that of the first radial supporting structure 211. That is to say, under the action of the same radial force (the sizes and the directions of radial acting forces and the acting time are all the same), the radial length variation of the first radial supporting structure 211 in the radial supporting section is less than that of the second radial supporting structure 221 at the same position; or under the action of the same radial force (the sizes and the directions of the radial acting forces and the acting time are all the same), the radial length change rate of the first radial supporting structure 211 in the radial supporting section is less than that of the second radial supporting structure 221 at the same position; and this change rate is a ratio of the radial length variation to an original radial length.

Under the action of the same radial force, a larger radial length variation or a larger radial length change rate indicates higher radial deformability and lower radial supportability of a radial supporting structure, and vice versa. Alternatively, in the above-mentioned maximum radial length region L, in case of the same radial change rate or the same radial variation, a radial external force exerted on the first radial supporting structure 211 is greater than the radial external force exerted on the second radial supporting structure 221. A higher radial force exerted on indicates a lower radial deformability and a higher radial supportability, and vice versa.

Figure 7:
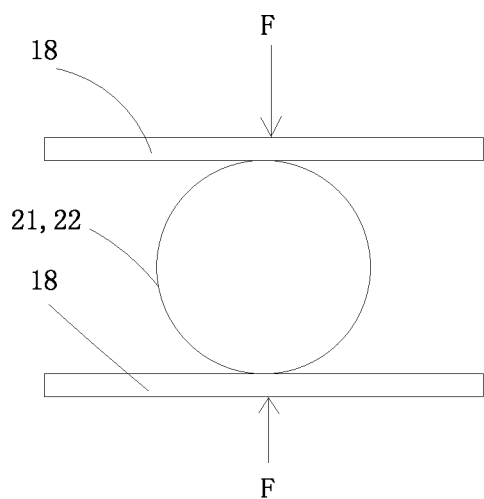
FIG. 7 is a schematic diagram of a flat plate pressing method-based test on a luminal stent graft according to a second embodiment of the present application.
Figure 8:
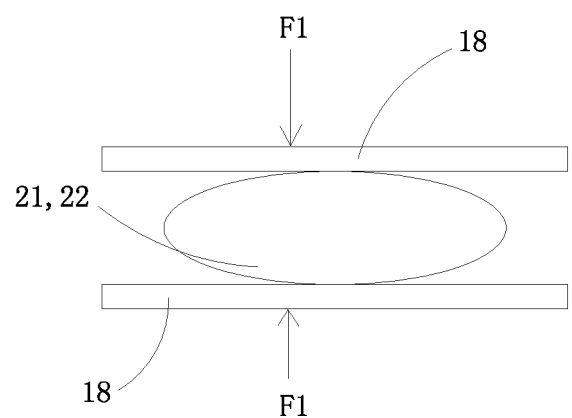
FIG. 8 is a schematic diagram of a flat plate pressing method-based test on the luminal stent graft according to the second embodiment of the present application.

With reference to FIG. 7, a flat plate pressing method may be adopted, namely the tubular bodies 21 and 22 may be clamped in the radial supporting section along a tangential direction of the circumference of the radial supporting section by adopting two mutually parallel flat plates 18. In a test process, the two flat plates are always kept in parallel. Equal radial forces F are applied to the flat plates 18 to test the radial length variations $\Delta R$ or the radial length change rates $\Delta R/R$ of the first radial supporting structure 211 and the second radial supporting structure 221 in the radial supporting section, and the directions of the radial forces F are parallel to certain diameters, which are located at pressed portions, of the tube bodies 21 and 22. Or, when the above-mentioned flat plate pressing method may be adopted to compress the first radial supporting structure 211 in the radial supporting section or the second radial supporting structure 221 in the radial supporting section from an original size R (FIG. 7) to R/2 (FIG. 8), a measured radial force F1 to be applied is used for evaluating the radial supporting force or the radial supportability, and this evaluation result is equivalent to an evaluation result obtained on the basis of the radial length variation or the radial length change rate, wherein in a situation of the same radial acting condition (the acting time and the acting way of the radial force are the same), a smaller value of the radial force F1 applied to compressing the tubular body from the original size R to R/2 indicates higher radial deformability and lower radial supportability of the tubular body, and vice versa.

The above-mentioned flat plate pressing method is only one example test method, and is not intended to be a limitation to the present application. A person of ordinary skill in the art can adopt any proper method to carry out a test equivalent to the flat plate pressing method, for example, a radial acting force also may be uniformly applied to the circumferential direction of the lumen for testing. To be specific, a radial supporting force tester RX550-100 of the Machine Solution Inc (MSI) Company may be adopted.

In one specific implementation mode of the present application, under the action of the same radial force, the radial length variation of the second radial supporting structure 221 in the radial supporting section is 1.05 times to 10 times the radial length variation of the first radial supporting structure 211 in the radial supporting section, and for example may be two to 5 times. Or, under the action of the same radial force, the radial length change rate of the second radial supporting structure 221 in the radial supporting section is 1.05 times to 10 times the radial length change rate of the first radial supporting structure 211 in the radial supporting section, and for example may be two to 5 times. Or, under the same test condition, the radial force to be applied to compressing the first radial supporting structure 211 from the original size R to R/2 is 1.05 times to 10 times the radial force to be applied to compressing the second radial supporting structure 221 from the original size R to R/2, and for example may be two to 5 times.

When compared with the first radial supporting structure 211, when the second radial supporting structure 221, has a radial deformability that is extremely high, its radial supportability is low, which leads to a situation that the second radial supporting structure may not be completely radially unfolded in a releasing process, thereby causing a wrinkling or collapsing phenomenon, so that the radial deformability of the second radial supporting structure 221 will not generally exceed 10 times of the radial deformability of the first radial supporting structure 211. Of course, if the radial deformability of the second radial supporting structure 221 has little difference from that of the first radial supporting structure 211, an endoleak still may be formed after the second tubular body 22 is implanted. Therefore, the radial deformability of the second radial supporting structure 221 is generally greater than 1.05 times of the radial deformability of the first radial supporting structure 211. To be specific, the radial deformability of the second radial supporting structure 221 is two to 5 times, such as 3 times and 4 times, the radial deformability of the first radial supporting structure 211.

It should be noted that the radial deformability described herein is a radial reacting force generated by a tubular body on an external radial acting force when the tubular body is pressed by the external radial acting force, for example, when the first tubular body 21 or the second tubular body 22 is pressed radially by a lumen after being implanted. Under the same external radial acting force, higher radial reacting force generated by the tubular body indicates that this tubular body has relatively low radial deformability and relatively high radial supporting force or relatively high radial supportability, and vice versa. For example, when the first radial supporting structure 211 and the second radial supporting structure 221 are implanted into the same position and are pressed radially by the same lumen, the radial reacting force generated by the first radial supporting structure 211 is relatively high, and the radial reacting force generated by the second radial supporting structure 221 is relatively low, so that the first radial supporting structure 211 has higher radial supporting force or higher radial supportability and lower radial deformability than the second tubular body 22. If a tubular body does not have the above-mentioned radial expandability by itself, for example the one which only has a graft and does not have a radial supporting structure, it will be compressed under the external radial acting force, but after the external force is withdrawn, it may not restore to its initial shape and keep the initial shape, so that the radial reacting force generated by this tubular body on the external radial acting force may be basically ignored, and it is unnecessary to compare the radial supporting force or the radial supportability of the tubular body of this structure.

In addition, the second radial supporting structure 221 is arranged along the circumferential direction, and further, the second radial supporting structure 221 is continuously arranged along the circumferential direction. After implantation, when a certain portion of the second radial supporting structure 221 deforms under the radial acting force, the second radial supporting structure 221 may transmit this deformation or pressure along the circumferential direction, thereby realizing that the second tubular body complies with the shape of the lumen wall and clings to the lumen wall, and the second radial supporting structure 221 may actively fill the small gaps around to avoid formation of a blood flow leak channel between the second tubular body and the lumen wall.

It can be known from the above description that after the luminal stent graft 2 is implanted into a human body lumen, in its radial supporting section, the luminal stent graft 2 includes the first tubular body 21 and the second tubular body 22 covering the first tubular body 21; the first tubular body 21 may cling to the lumen wall due to its relatively low radial deformability, so that the whole luminal stent graft may be fixed in the lumen to avoid displacement or falling off from the lumen; the second tubular body 22 has the radial supporting force due to the second radial supporting structure 221, and may be radially expanded to be attached to the lumen wall, so that no clearance will be formed between the lumen wall and the second tubular body 22 by insufficient radial supporting force. Furthermore, as the radial deformability of the second tubular body 22 is higher than that of the first tubular body 21, when the second tubular body 22 and the first tubular body 21 are implanted into the same lumen position at the same time, the second tubular body 22 complies with the shape deformation of the inner wall of the lumen more easily, thereby avoiding formation of the clearance between the second tubular body 22 and the inner wall of the lumen and cutting off a channel or an opening that may form the type-I endoleak.

For example, with reference to FIG. 9, in a natural state, namely a state that no external radial force or external radial pressure exists, the first tubular body 21 (namely the first radial supporting structure) and the second tubular body 22 (namely the second radial supporting structure) may be both radially expanded and unfolded. With reference to FIG. 10, under the external radial force or external radial pressure, for example, when the luminal stent graft is placed at a certain portion of a to-be-treated blood vessel, the first tubular body 21 will keep the radial shape basically unchanged under the radial pressure of the vascular wall to avoid displacement or falling off of the luminal stent graft 2; and the second tubular body 22 will comply with the deformation under the radial pressure of the blood vessel and keep radial expansion and unfolding to avoid deformation such as radial collapse, sinking, and turnover.

With reference to FIG. 11, if the luminal stent graft 2 is implanted into a lumen having a plaque 13, under a radial force or radial pressure generated by the lumen, the first tubular body 21 keeps the radial shape basically unchanged to avoid displacement or falling off, and maintains a blood flow channel unblocked; the second tubular body 22 may comply with the deformation at the plaque 13, and is still attached to the inner wall of the lumen and the surface of the plaque by its radial expandability, so that the clearance formed between the first tubular body 21 and the inner wall of the lumen is filled, and at the same time, no clearance will be formed among the second tubular body 22, the inner wall of the lumen and the surface of the plaque, thus cutting off the channel or the opening that may form the type-I endoleak and avoiding the blood from flowing into a tumor body or a dissection 18.

Third Embodiment

With reference to FIG. 12, the difference from the luminal stent graft of the first embodiment is that the tube orifice, which is close to the proximal end 23, of a second tubular body 22 of a luminal stent graft 2 according to the third embodiment is hermetically connected with the peripheral surface of a first tubular body 21, thus forming a closed tube orifice, and the tube orifice, which is close to the distal end 24, of the second tubular body 22 is open. The second tubular body 22 is located near to the proximal end 23 of the first tubular body 21, but a person of ordinary skill in the art should know that this figure is only used as an example and is not a limitation to the present application. A person of ordinary skill in the art can arrange the second tubular body 22 near to the distal end 24 of the first tubular body 21 based on the instruction of the present application.

Figure 13B:
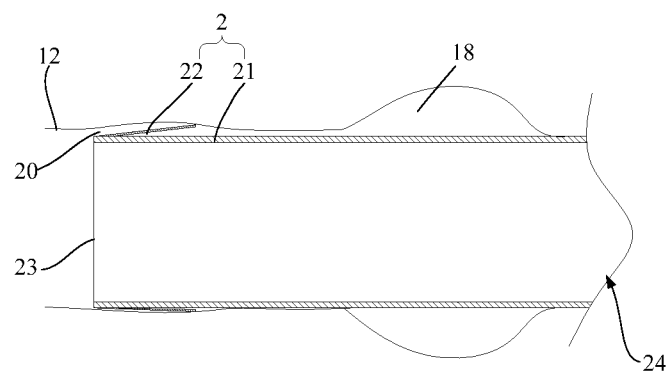
FIG. 13B is an axial section diagram of the luminal stent graft, which is implanted into a lumen, in FIG. 13A.

With reference to FIG. 13A and FIG. 13B, to be specific, the second tubular body 22 may further include a straight tube section 221a, a conical tube section 222a and a connecting section 223a; the connecting section 223a is sealingly connected with the first tubular body 21; the conical tube section 222a is connected with the connecting section 223a and the straight tube section 221a; and the maximum radial length region of the second tubular body is located in the straight tube section 221a, so that a second radial supporting structure (which is not shown in the figure) is at least arranged in the straight tube section 221a.

After implantation, the second tubular body 22 complies with the deformation of the inner wall of a lumen 12; the connecting section 223a and the conical tube section 222a may possibly form a clearance 20 together with the inner wall of the lumen 12 as their radial lengths are relatively small; the straight tube section 221a has a relatively large radial length, and may be completely attached to the inner wall of the lumen 12 through the second radial supporting structure; if the shape of a certain position, where the straight tube section 221a is implanted, on the wall of the lumen 12 is not smooth, the straight tube section 221a may comply with the shape deformation, but other portions of the straight tube section 221a still may be attached to the inner wall of the lumen 12 by their radial expandability. When flowing into the luminal stent graft 2, blood flows into the clearance 20 possibly formed by the connecting section 223a and the conical tube section 222a together with the inner wall of the lumen 12 at the same time, or also may flow into a clearance (which is not shown in the figure in detail) formed by the straight tube section 221a and the inner wall of the lumen 12. However, the portion, which is attached into the lumen 12, of the straight tube section 221a will prevent further inflow of the blood by its radial supporting force, and the blood left in all the above-mentioned clearances are thrombosed, and then forms a seal, thereby cutting off a channel or an opening that may form type-I endoleak and avoiding the blood from flowing into a tumor body or a dissection 18.

Fourth Embodiment

Figure 14:
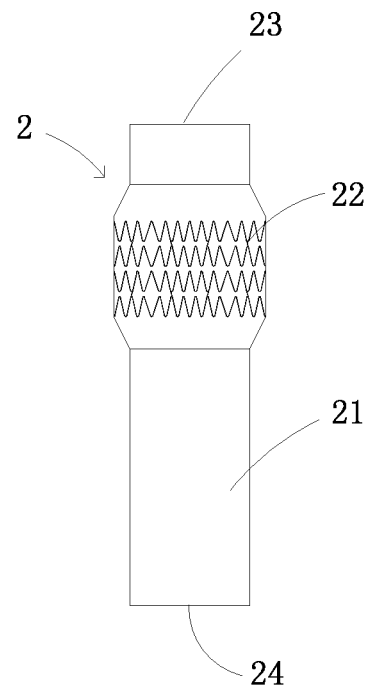
FIG. 14 is a schematic diagram of a luminal stent graft according to a fourth embodiment of the present application.

With reference to FIG. 14, the difference from the luminal stent graft of the first embodiment is that two tube orifices of a second tubular body 22 of a luminal stent graft 2, according to the fourth embodiment, are both sealingly connected with the peripheral surface of a first tubular body 21, thus forming two closed tube orifices. At the moment, if the two tube orifices of the second tubular body 22 are sealed, this luminal stent graft is similar to that of the second embodiment, and similarly, after implantation, a channel or an opening that may form type-I endoleak also may be cut off. In this sealing process, no other sealing or filling materials need to be added into the luminal stent graft 2 in advance or after the luminal stent graft 2 is implanted, but sealing may be realized only through inflowing blood from normal blood circulation, so that no extra biological risk caused by the sealing or filling materials will be increased.

Fifth Embodiment

Figure 15:
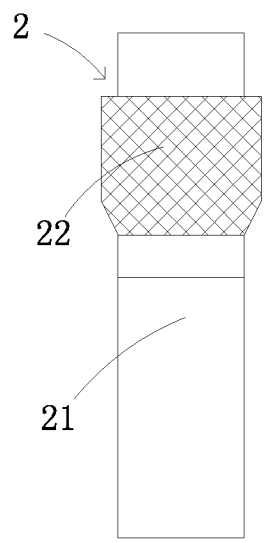
FIG. 15 is a schematic diagram of an example structure of a luminal stent graft according to a fifth embodiment of the present application.
Figure 16:
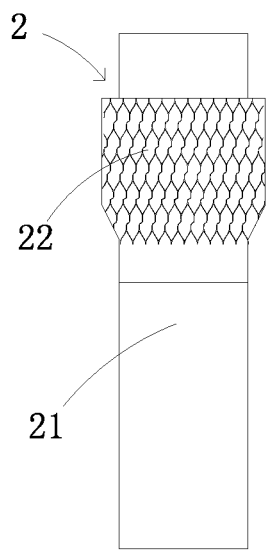
FIG. 16 is a schematic diagram of another example structure of a luminal stent graft according to the fifth embodiment of the present application.

A luminal stent graft of the fifth embodiment is approximately the same as the luminal stent graft of the first embodiment, but the difference is that a second radial supporting structure includes a mesh structure, for example a woven mesh structure or a cut mesh structure. For example, with reference to FIG. 15, the radial supporting structure of a second tubular body 22 includes the woven mesh structure; and with reference to FIG. 16, the radial supporting structure of the second tubular body 22 includes the cut mesh structure.

Figure 17:
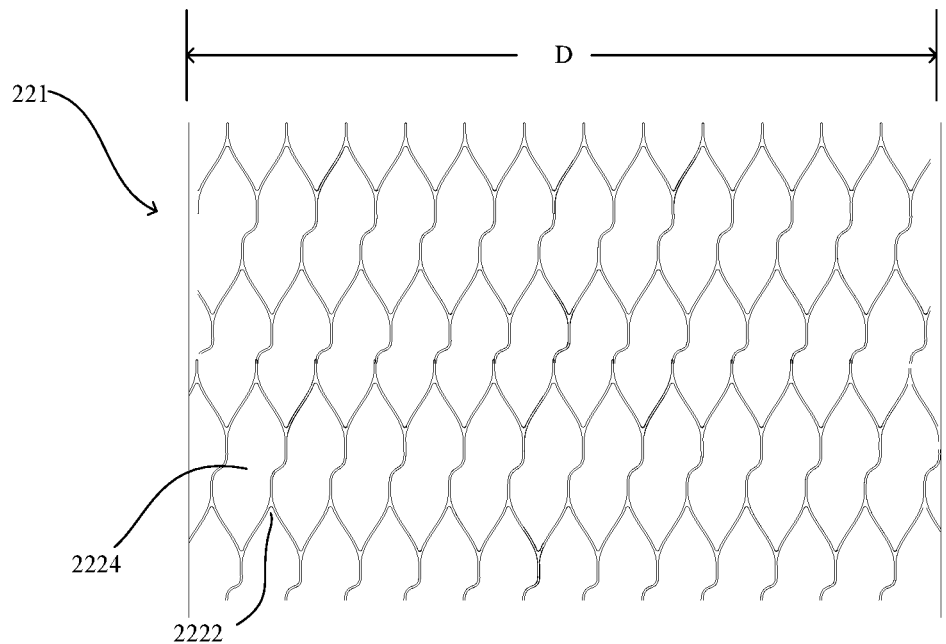
FIG. 17 is a schematic diagram of a cut meshed structure of the second tubular body in FIG. 16.
Figure 18:
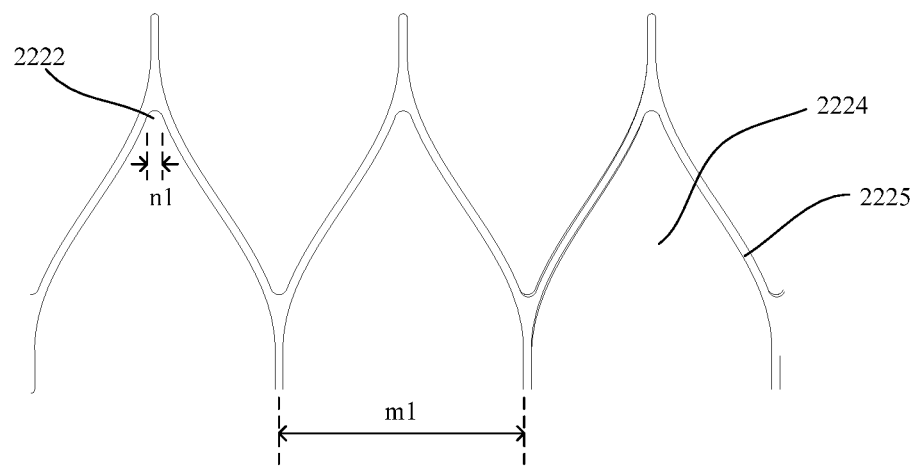
FIG. 18 is a partial enlarged view of FIG. 17.

With reference to FIG. 17 and FIG. 18, the second radial supporting structure 221 includes the cut mesh structure which has multiple grids 2224. The mesh structure may be formed by cutting a metal net tube, for example it may be integrally formed by carrying out laser cutting on a memory alloy (including a nickel-titanium alloy) net tube, and the metal net tube may be 0.05 mm to 0.4 mm in thickness. During cutting, the diameter of each of connecting rods 2225 forming the grids 2224 in an encircling manner may be 0.05 mm to 0.4 mm. To be specific, when the radial length of the second radial supporting structure 221 is 4 mm to 20 mm, the diameter of each connecting rod 2225 is 0.05 mm to 0.32 mm; when the radial length of the second radial supporting structure 221 is 20 mm to 50 mm, the diameter of each connecting rod 2225 is 0.1 mm to 0.35 mm; and when the radial length of the second radial supporting structure 221 is 50 mm to 80 mm, the diameter of each connecting rod 2225 is 0.2 mm to 0.4 mm. As a metal wire within the above-mentioned wire diameter range has relatively high bending flexibility, a waveform ring-like object formed by winding the metal wire has relatively high radial deformability. The maximum width m1 of any grid 2224 formed by cutting and the perimeter D of the second tubular body 22 at this grid 2224 accord with a condition that m1 is less than or equal to D/12. To be specific, when the radial length of the second radial supporting structure 221 is 4 to 20 mm, the maximum width m1 and the perimeter D accord with the condition that m1 is less than or equal to D/12, and m1 ranges from 1.5 mm to 5 mm. When the radial length of the second radial supporting structure 221 is 20 mm to 50 mm, the maximum width m1 and the perimeter D accord with a condition that m1 is less than or equal to D/13, and m1 ranges from 1.5 mm to 7 mm. When the radial length of the second radial supporting structure 221 is 50 mm to 80 mm, the maximum width m1 and the perimeter D accord with a condition that m1 is less than or equal to D/14, and m1 ranges from 1.5 mm to 8 mm. If m1 is smaller, the filling effect is better.

To further improve the deformability of the second radial supporting structure for complying with the inner wall of the lumen, the maximum length of the above-mentioned grid along an axial direction is 4 mm to 16 mm. To be specific, when the radial length of the second radial supporting structure 221 is 4 mm to 20 mm, the maximum length of the grid along the axial direction is 4 to 12 mm. When the radial length of the second radial supporting structure 221 is 20 mm to 50 mm, the maximum length of the grid along the axial direction is 6 mm to 14 mm. When the radial length of the second radial supporting structure 221 is 50 mm to 80 mm, the maximum length of the grid along the axial direction is 8 mm to 16 mm.

At least one grid 2224 of the meshed structure has an internal fillet 2222, the maximum width n1 of the internal fillet 2222 along the circumferential direction accords with a condition that n1 is less than or equal to 1.5 mm. If the n1 value is smaller, the deformability of the second tubular body 22 for complying with the inner wall of the lumen is higher, and the clearance filling capacity is higher, so that the capacity of blocking the endoleak is higher.

Sixth Embodiment

The sixth embodiment provides a luminal stent graft system. The luminal stent graft system includes at least one luminal stent graft 2 according to any one of embodiments 1 to 4, where multiple luminal stent grafts 2 may be implanted into a lumen cooperatively, or one or multiple luminal stent grafts 2 and other existing luminal stent grafts which do not have second radial supporting structures are implanted into the lumen cooperatively. In order to facilitate distinguishing various embodiments, the luminal stent grafts 2 according to the embodiments of the present application are collectively called a first luminal stent graft 2 below, and the other existing luminal stent grafts which do not have the second radial supporting structures may be collectively called a second luminal stent graft 3. There is at least one first luminal stent graft 2, namely there may be one or two first luminal stent grafts, and even more first luminal stent grafts. For example, one conventional second luminal stent graft 3 and one first luminal stent graft 2 according to the embodiment of the present application may be cooperatively applied to a chimney technology, or a periscope technology, or a sandwich technology, for example. For another example, one conventional second luminal stent graft 3 and two first luminal stent grafts 2 according to the embodiments of the present application may be cooperatively applied to an abdominal aorta, wherein the second luminal stent graft 3 is implanted into the abdominal aorta, and the two first luminal stent grafts 2 are respectively implanted into a renal artery. The above situations are only used as examples, and are not limitations to the present application, so that persons of ordinary skill in the art can select a proper number of and a proper type of luminal stent grafts to form the luminal stent graft system for cooperative implantation according to a specific condition of an implantation lumen based on the instruction of the present application to guarantee unblocked blood flow.

Figure 19:
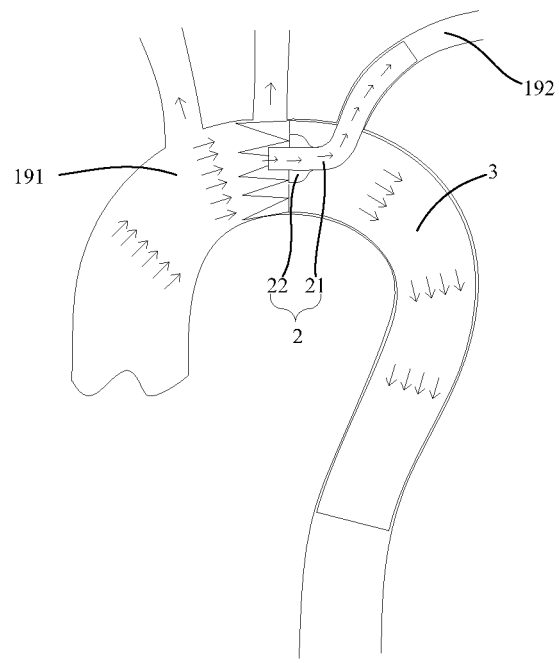
FIG. 19 is a schematic diagram of a luminal stent graft system according to a sixth embodiment of the present application.
Figure 20:
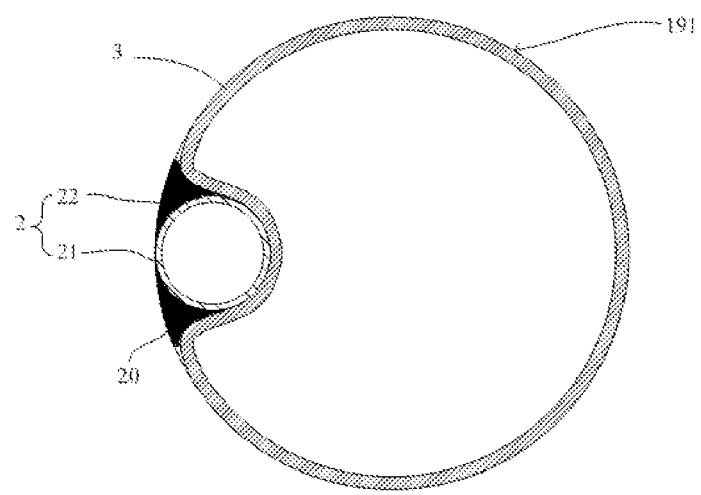
FIG. 20 is a radial section diagram of the proximal end of the luminal stent graft system in FIG. 19.

With reference to FIG. 19, the aorta arch 191 generally has three branch blood vessels, for example, a blood flow channel may be rebuilt at this position by adopting the chimney technology. An arrow is used in the figure to provide a blood flow direction, and it has been defined that the blood flows goes from the proximal end to the distal end in the above contents. After implantation, with reference to FIG. 20 together, directions of openings in the proximal end of the first luminal stent graft 2 and the proximal end of the second luminal stent graft 3 are consistent, and the first luminal stent graft 2 and the second luminal stent graft 3 are arranged in the aorta arch blood vessel 191 side by side, wherein the first luminal stent graft 2 is a luminal stent graft which has a first tubular body 21 and a second tubular body 22 according to the embodiment of the present application; the second luminal stent graft 3 may be one of the first luminal stent graft 2, and also may be an existing luminal stent graft which does not have a second radial supporting structure. In this figure, the second luminal stent graft 3 is a conventional stent graft, for example, it is may be a straight tubular stent graft. The distal end of the first luminal stent graft 2 extends into one branch blood vessel, such as a left subclavian artery 192, so that blood can flow into the branch blood vessel from the aorta arch blood vessel 191 through the first luminal stent graft 2, thus rebuilding a branch blood vessel channel. As a brief schematic, FIG. 20 shows the first luminal stent graft 2 including the first tubular body 21 and the second tubular body 22, wherein the second tubular body 22 covers part of a proximal end region of the first tubular body 21, but does not cover the proximal end face of the first tubular body 21; and the specific structure of the first luminal stent graft 2 is as shown in FIG. 3. The proximal end of the first luminal stent graft 2 and the proximal end of the second luminal stent graft 3 are arranged side by side; the proximal end face of the second tubular body 22 is substantially flush with the proximal end face of the second luminal stent 3; and the first tubular body 21 relatively extends and protrudes towards the proximal end.

With reference to FIG. 20, after implantation, and under the radial compression action of the lumen wall, the first luminal stent graft 2 and the proximal end region of the second luminal stent graft 3 radially press each other in the aorta arch blood vessel 191; in the radial supporting section, the second luminal stent graft 3 serving as a main body stent complies with the deformation under the pressure of the first luminal stent graft 2 serving as a branch stent; to guarantee unblocked blood flow in the branch blood vessel, the first tubular body 21 of the first luminal stent graft 2 has relatively high radial supporting force, and may avoid lumen loss in a pressing process; and the second tubular body 22 may simultaneously comply with the shape deformation of the lumen wall and the shape deformation of the second luminal stent graft 3 due to its relatively low radial supporting force, thereby forming a clearance 20 between the first tubular body 21 and the second tubular body 22. A type-I endoleak channel between the main body stent and the branch stent in the prior art is filled with the clearance 20; as one end of the clearance 20 is open, and the other end of the clearance 20 is closed, blood flow flowing into the clearance 20 may be used as a sealing and filling material for blocking the type-I endoleak channel to avoid the blood flow from entering a tumor body or a dissection; and the second tubular body 22 is unblocked, so that the blood flow can successfully flow into the branch blood vessel. Further, when the blood flow rushes at the semi-closed clearance 20, a vortex is formed under the action of the pressure, and then the blood flow direction is changed, so that the blood can flow into the first tubular body 21 favorably, thereby promoting unblocked circulation of the blood flow in the branch blood vessel and guaranteeing the flow rate of the blood flow in the branch blood vessel.

With reference to FIG. 21, in another example, the blood vessel channel may be rebuilt by adopting the periscope technology. The distal end of the second luminal stent graft 3 serving as the main body stent and the proximal end of the first luminal stent graft 2 serving as the branch stent may be arranged side by side; an arrow in the figure shows a blood flow direction; for a single luminal stent graft here, blood always flows from the proximal end of the luminal stent graft to the distal end. To be specific, the first luminal stent graft 2 includes a first tubular body 21 and a second tubular body 22; the second tubular body 22 covers part of a proximal end region of the first tubular body 21, but does not cover the proximal end face of the first tubular body 21. The proximal end of the first luminal stent graft 2 and the distal end of the second luminal stent graft 3 are arranged side by side; the proximal end face of the second tubular body 22 is basically flush with the distal end face of the second luminal stent graft 3; and the first tubular body 21 extends and protrudes relative to the second tubular body 22. After implantation, under the radial compression action of a lumen (such as an aorta arch 191) wall, a semi-closed clearance (which is not shown in the figure) is formed among the distal end of the second luminal stent graft 3, the first tubular body 21, the second tubular body 22 and the lumen wall, and a semi-closed clearance (which is not shown in the figure) is also formed between the first tubular body 21 and the second tubular body 22, thereby preventing generation of a type-I endoleak channel and avoiding blood from flowing into a tumor body or a dissection. In addition, the blood flow may inversely enter the proximal end of the first luminal stent graft 2 from the distal end of the second luminal stent graft 3, as shown in the arrow A. Also, in this case, the blood flow generates relatively low impact force on the above-mentioned semi-closed clearances, thus further preventing formation of type-I endoleak.

Seventh Embodiment

With reference to FIG. 22, the luminal stent graft according to the embodiment of the present application also may be applied to an abdominal aorta 193. If the stent is implanted into the abdominal aorta 193, two branch blood vessels at a renal artery and/or an iliac artery should be considered according to the shape of a tumor body or a dissection 18. An arrow in the figure is a blood flow direction, and it has been defined above that for a single luminal stent graft, blood flow flows from the proximal end to the distal end. Multiple first luminal stent grafts 42 and 43 and one second luminal stent graft 41 may be adopted for cooperative implantation, wherein the first luminal stent grafts 42 and 43 are luminal stent grafts having first tube bodies and second tube bodies according to the embodiments of the present application, and the second luminal stent graft 41 may be a luminal stent graft which is of the same type as the first luminal stent grafts 42 and 43 or may be a different luminal stent graft. In this figure, the second luminal stent graft 41 is a conventional covered stent, such as a straight tube type covered stent.

With reference to FIG. 22 and FIG. 23, at renal arteries 194 and 195, the two first luminal stent grafts 42 and 43 and the one second luminal stent graft 41 are implanted cooperatively; directions of openings in the proximal ends of the two first luminal stent grafts 42 and 43 and the proximal end of the second luminal stent graft 41 are consistent, and the first luminal stent grafts 42 and 43 and the second luminal stent graft 41 are arranged in the abdominal aorta blood vessel 193 side by side; the distal end of each of the two first luminal stent grafts 42 and 43 extends into one branch blood vessel respectively, namely the right renal artery 194 or the left renal artery 195, so that blood may flow into the branch blood vessels from the abdominal aorta blood vessel 193 through the first luminal stent grafts 42 and 43.

To be specific, the first luminal stent graft 42 includes a first tubular body 421 and a second tubular body 422; the second tubular body 422 covers part of a proximal end region of the first tubular body 421, but does not cover the proximal end face of the first tubular body 421. The proximal end of the first luminal stent graft 42 and the proximal end of the second luminal stent graft 41 are arranged side by side; the proximal end face of the second tubular body 422 is basically flush with the proximal end face of the second luminal stent graft 41; and the first tubular body 421 relatively extends and protrudes towards the proximal end. Similarly, the first luminal stent graft 43 includes a first tubular body 431 and a second tubular body 432; the second tubular body 432 covers part of a proximal end region of the first tubular body 431, but does not cover the proximal end face of the first tubular body 431. The proximal end of the first luminal stent graft 43 and the proximal end of the second luminal stent graft 41 are arranged side by side; the proximal end face of the second tubular body 43 is basically flush with the proximal end face of the second luminal stent graft 41; and the first tubular body 431 relatively extends and protrudes towards the proximal end.

With reference to FIG. 23, after implantation, under the radial compression action of the lumen wall of the abdominal aorta blood vessel 193, the first luminal stent graft 42 and the proximal end region of the second luminal stent graft 41 radially press each other in the abdominal aorta blood vessel 193; in the radial supporting section, the second luminal stent graft 41 serving as a main body stent complies with the deformation under the pressure of the first luminal stent graft 42 serving as a branch stent; to guarantee unblocked blood flow in the branch blood vessel, the first tubular body 421 of the first luminal stent graft 42 has relatively high radial supporting force, and may avoid lumen loss in a pressing process; and the second tubular body 422 may comply with the shape deformation of the lumen wall and the shape deformation of the second luminal stent graft 41 due to its relatively low radial supporting force, thereby forming a clearance 420 between the first tubular body 421 and the second tubular body 422. A type-I endoleak channel between the main body stent and the branch stent in the prior art is filled with the clearance 420; as one end of the clearance 420 is open, and the other end of the clearance 420 is closed, blood flow flowing into the clearance 420 may be used as a sealing and filling material for plugging the type-I endoleak channel; and the second tubular body 422 is unblocked, so that the blood flow may successfully flow into the branch blood vessel. Further, when the blood flow rushes at the semi-closed clearance 420, a vortex is formed under the action of the pressure, and then the blood flow direction is changed, so that the blood may flow into the first tubular body 421 favorably, thereby promoting unblocked circulation of the blood flow in the branch blood vessel and guaranteeing the flow rate of the blood flow in the branch blood vessel. Similarly, a clearance 430 may be also formed between the first tubular body 431 and the second tubular body 432 of the first luminal stent graft 43, and the type-I endoleak channel between the main body stent and the branch stent in the prior art is filled with the clearance 430.

With reference to FIG. 22 and FIG. 24, at iliac arteries 196 and 197, the two first luminal stent grafts 44 and 45 are implanted cooperatively; directions of openings in the proximal ends of the two first luminal stent grafts 44 and 45 are consistent, and the first luminal stent grafts 44 and 45 are arranged in the abdominal aorta blood vessel 193 side by side; the distal end of each of the two first luminal stent grafts 44 and 45 extends into one branch blood vessel respectively, namely the right iliac artery 196 or the left iliac artery 197, so that blood may flow into the branch blood vessels 196 and 197 from the abdominal aorta blood vessel 193 through the first luminal stent grafts 44 and 45.

To be specific, the first luminal stent graft 44 includes a first tubular body 441 and a second tubular body 442; the second tubular body 442 covers part of a proximal end region of the first tubular body 441, but does not cover the proximal end face of the first tubular body 441. The first luminal stent graft 45 includes a first tubular body 451 and a second tubular body 452; the second tubular body 452 covers part of a proximal end region of the first tubular body 451, but does not cover the proximal end face of the first tubular body 451. The proximal ends of the two first luminal stent grafts 44 and 45 are arranged side by side, and their proximal end faces are basically flush with each other, for example, the proximal end faces of the two first tube bodies 441 and 451 are basically flush with each other, and/or the proximal end faces of the two second tube bodies 442 and 452 are basically flush with each other.

With reference to FIG. 24, after implantation, under the radial compression action of the lumen wall of the abdominal aorta blood vessel 193, the two first luminal stent grafts 44 and 45 radially press each other in the abdominal aorta blood vessel 193; in the radial supporting section, the two first tube bodies 441 and 451 deform little due to their relatively high radial supporting forces, and the two second tube bodies 442 and 452 may comply with the shape deformation of the lumen wall and the shape deformation of the first tube bodies due to relatively low radial supporting force, thereby forming clearances, such as clearances 440 and 450, between the corresponding first tube bodies and the corresponding second tube bodies. As one end of each clearance is open, and the other end of the clearance is closed, blood flow flowing into the clearance may be used as a sealing and filling material for plugging a type-I endoleak channel to avoid the blood from flowing into the a tumor body or a dissection and ensure that the blood flow may successfully flow into the two first tube bodies.

Eighth Embodiment

Figure 25:
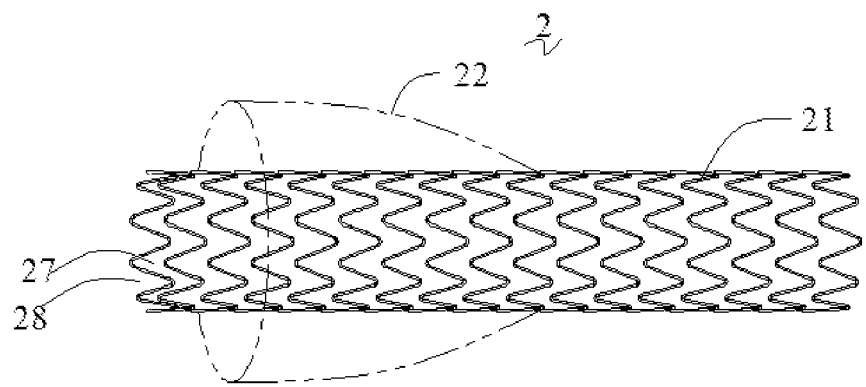
FIG. 25 is a schematic diagram of a luminal stent graft provided by an eighth embodiment of the present application.

With reference to FIG. 25, a luminal stent graft 2 according to the seventh embodiment of the present application is approximately similar to the luminal stent graft 2 of the first embodiment of the present application, and includes a first tubular body 21 and a second tubular body 22. The second tubular body 22 is sleeved outside the first tubular body 21, and covers at least one portion of the first tubular body 21; and one end of the second tubular body 22 is sealingly connected with the peripheral surface of the first tubular body 21. The difference between the luminal stent graft 2 of this embodiment and the luminal stent graft 2 of the first embodiment is as follows: each end of the first tubular body 21 of the eighth embodiment has multiple convex pieces 27 extending in parallel to the longitudinal axis of the first tubular body 21, and a gap 28 is reserved between two adjacent convex pieces 27. The convex pieces 27 may be formed in a way of, for example, removing the graft between two adjacent wave crests in a wave loop, which is closest to the end portion of the first tubular body 21, of the first tubular body 21 in the first embodiment. The wave loop in the present application is a waveform ring-like object surrounding the longitudinal central axis of the first tubular body 21.

After the luminal stent graft 2 in this embodiment is implanted into a human body by adopting a method as shown in FIG. 19, FIG. 21 or FIG. 22, even if the side wall of the blood flow inlet end of the first tubular body 21 in this embodiment is gathered together into the lumen in a blood vessel due to the pressure applied by the main body stent graft and the vascular wall, the blood flow also may flow into the first tubular body 21 from the gap 28 between the two convex pieces 27 at the blood flow inlet end of the first tubular body 21 in this embodiment, thereby avoiding the risk that the blood flow may not enter a corresponding branch blood vessel from the blood flow inlet end of the first tubular body which is closed by the pressure of the main body stent graft and the vascular wall, and improving the safety and the effectiveness of the operation. It should be noted that in other embodiments, for example, a hole is formed in the graft (for example: the graft between the first wave loop counted from left to right and the blood flow inlet end or the graft between the first wave loop counted from left to right and the second wave loop) near to the blood flow inlet end (namely the left side end of the first tubular body 21 in FIG. 3) of the first tubular body 21 as shown in FIG. 3, and penetrates through the graft, or the first wave loop, which is close to the blood flow inlet end (namely the left side end of the first tubular body 21 in FIG. 3), of the first tubular body 21 as shown in FIG. 3 is not completely covered by the graft (namely multiple wave crests, which face to the left side, of the first wave loop counted from left to right are exposed); and it also ensures that even under a condition that an inlet of the blood flow inlet end is blocked by a blood vessel, there is still a blood flow flowing towards a branch blood vessel through the first tubular body.

It should be noted that in FIG. 25, to display the structure of the first tubular body 21 more clearly, a simple dotted line is specially adopted to express the second tubular body 22. As a matter of fact, the second tubular body 22 in this embodiment is the same as the second tubular body 22 in the first embodiment, and the first tubular body 21 in this embodiment is approximately similar to the first tubular body 21 in the first embodiment, but the difference is as follows: two ends of the first tubular body 21 in this embodiment have multiple convex pieces 27, that is to say, the first tubular body 21 in this embodiment may be obtained by removing a film between every two adjacent wave crests in a wave loop, which is closest to the corresponding end portion, at each of two ends of the first tubular body 21 in the first embodiment, namely the luminal stent graft 2 in this embodiment may be obtained by removing the film between every two adjacent wave crests in the wave loop, which is closest to the corresponding end portion, at each end of the first tubular body 21 of the luminal stent graft 2 in the first embodiment.

It can be understood that in other embodiments, according to an actual requirement, multiple convex pieces 27 may be only formed at the blood flow inlet end of the first tubular body 21. That is to say, no convex pieces 27 are arranged at the blood flow outlet end of the first tubular body 21.

It also can be understood that in other embodiments, a graft between one pair of adjacent wave crests in a wave loop, which is closest to the blood flow inlet end, of the first tubular body 21 in the first embodiment may not be removed according to a requirement as long as grafts between at least two pairs of adjacent wave crests in the multiple wave crests are removed to form the multiple convex pieces. It also can be understood that in other embodiments, at least one hole penetrating through each convex piece also may be formed in the convex piece. It also can be understood that in other embodiments, the wave crests of the convex pieces also may not be covered by the graft, and this may be designed according to an actual requirement.

Ninth Embodiment

Figure 26:
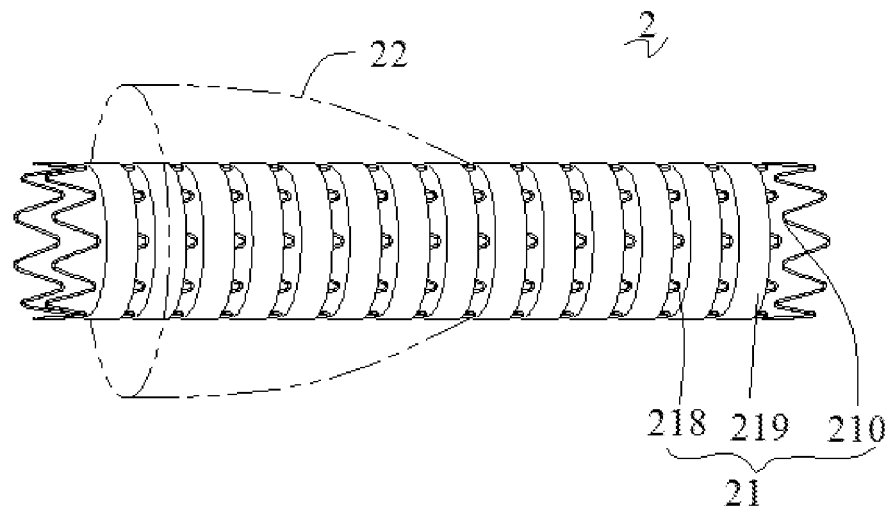
FIG. 26 is a schematic diagram of a luminal stent graft provided by a ninth embodiment of the present application.
Figure 27:
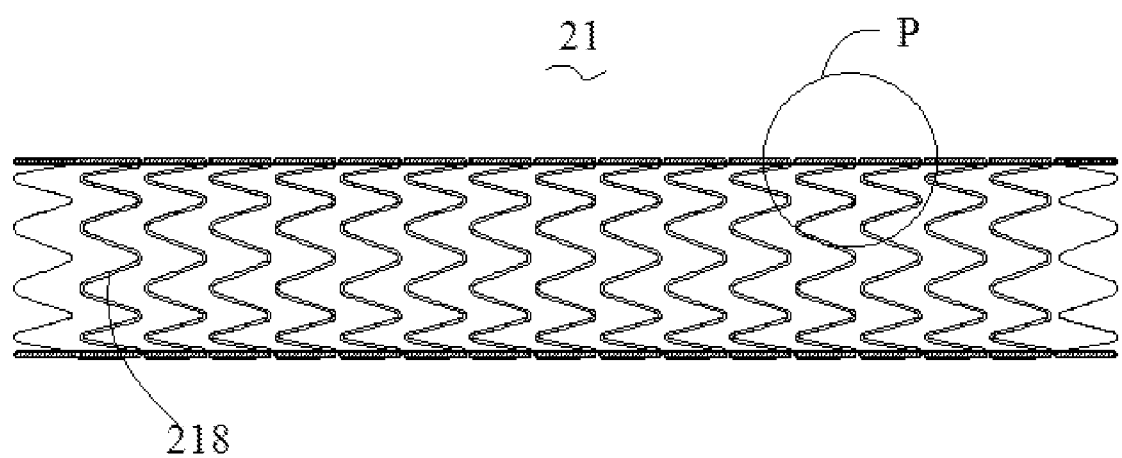
FIG. 27 is a schematic diagram of a first tubular body in FIG. 26.
Figure 28:
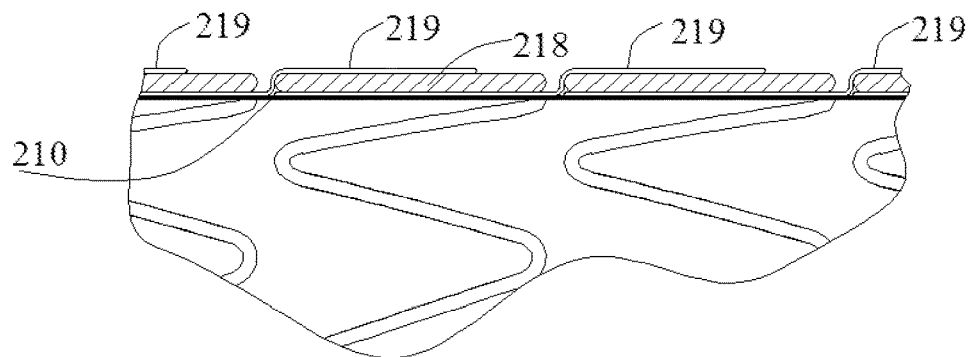
FIG. 28 is an enlarged view of a portion P in FIG. 27.

With reference to FIG. 26, a luminal stent graft 2 according to the ninth embodiment of the present application is approximately similar to the luminal stent graft 2 of the seventh embodiment of the present application, and includes a first tubular body 21 and a second tubular body 22. The second tubular body 22 is sleeved outside the first tubular body 21, and covers at least one portion of the first tubular body 21; and one end of the second tubular body 22 is sealingly connected with the peripheral surface of the first tubular body 21. The difference between the luminal stent graft 2 of the ninth embodiment of the present application and the luminal stent graft in the eighth embodiment is as follows: except for wave loops at two end sockets, each turn of wave loop 23 of the first tubular body 21 in this embodiment is arranged between one annular outer graft 219 and one barrel-shaped inner graft 210 in a clamping manner; moreover, the wave crests of each wave loop 218 are exposed outside, and the wave troughs of each wave loop 218 are all wrapped by the corresponding annular outer graft 219 and the corresponding barrel-shaped inner graft 210 (with reference to FIG. 27 and FIG. 28). The annular outer grafts 219 and the barrel-shaped inner grafts 210 may be PET (polyethylene terephthalate) films or PTFE (polytetrafluoroethylene) films, and may clamp the wave loops of the first tubular body 21 in a suturing or hot melting way.

Figure 29:
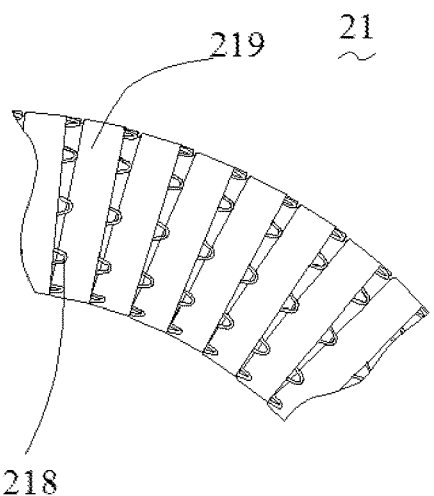
FIG. 29 is a diagram of a state after the first tubular body in FIG. 26 is bent.

With reference to FIG. 29, as the wave crests of each wave loop are exposed outside (that is to say, the wave crests of each wave loop are not wrapped by the annular outer graft 219 and the barrel-shaped inner graft 210), the wave crests of each wave loop may be separated from the annular outer graft 219 and the barrel-shaped inner graft 210 (that is to say, the wave crests of each wave loop may be up-warped relative to the annular outer graft 219 and the barrel-shaped inner graft 210); therefore, when the first tubular body 21 is bent, on the lesser curvature side, in two adjacent wave loops, one wave loop may be overlapped with the other wave loop, thereby improving the softness of the first tubular body 21. In the present application, the lesser curvature side is the side having a small bending radius when the first tubular body 21 is bent. In addition, it is precisely because the wave crests on the lesser curvature side are exposed outside that it is difficult for the wave crests on the lesser curvature side to puncture the barrel-shaped inner grafts in the bending process, thus prolonging the service life of the first tubular body 21.

It can be understood that in other embodiments, the wave crests on the lesser curvature side of the first tubular body 21 also may be only exposed to achieve the aim of the present application.

Tenth Embodiment

Figure 30:
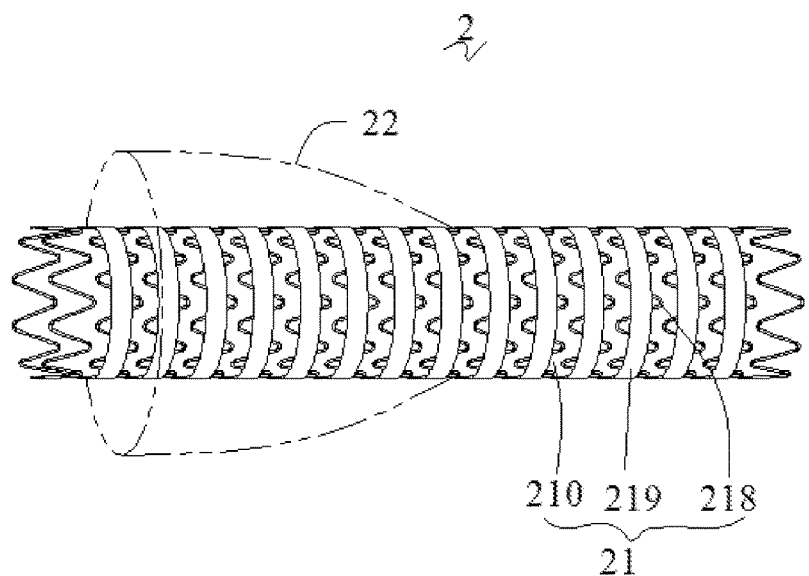
FIG. 30 is a schematic diagram of a luminal stent graft provided by a tenth embodiment of the present application.

With reference to FIG. 30, a luminal stent graft 2 according to the tenth embodiment of the present application is approximately similar to the luminal stent graft 2 of the eighth embodiment of the present application, and includes a first tubular body 21 and a second tubular body 22. The second tubular body 22 is sleeved outside the first tubular body 21, and covers at least one portion of the first tubular body 21; and one end of the second tubular body 22 is sealingly connected with the peripheral surface of the first tubular body 21. The difference between the luminal stent graft 2 of the tenth embodiment of the present application and the luminal stent graft in the eighth embodiment is as follows: except for wave loops at two end sockets, each turn of wave loop 218 of the first tubular body 21 in this embodiment is arranged between one annular outer graft 219 and one barrel-shaped inner graft 210 in a clamping manner, and the annular outer graft 219 is located between the wave crests and the wave troughs of the wave loop 218 clamped by it; and the wave crests and the wave troughs of the wave loop 218 are all exposed outside. The annular outer grafts 219 and the barrel-shaped inner grafts 210 may be PET films or PTFE films, and may clamp the wave loops of the first tubular body 21 in a suturing or hot melting way.

As the wave crests and the wave troughs of each wave loop are exposed outside (that is to say, the wave crests and the wave troughs of each wave loop are not wrapped by the annular outer graft 219 and the barrel-shaped inner graft 210), the wave crests and the wave troughs of each wave loop may be separated from the annular outer graft 219 and the barrel-shaped inner graft 210 (that is to say, the wave crests and the wave troughs of each wave loop may be all up-warped relative to the annular outer graft 219 and the barrel-shaped inner graft 210). Therefore, when the first tubular body 21 is bent, on the lesser curvature side, in two adjacent wave loops, one wave loop may be overlapped with the other wave loop, thereby improving the softness of the first tubular body 21. In addition, it is precisely because the wave crests and the wave troughs of the wave loops are exposed outside that it is difficult for the wave crests or the wave troughs of the wave loops to puncture the barrel-shaped inner grafts in the bending process, thus prolonging the service life of the first tubular body 21.

In one embodiment, the width of each annular outer graft 219 along the longitudinal central axial line direction of the first tubular body 21 is greater than or equal to ⅓ of a distance between the wave crests and the wave troughs of the wave loop clamped by the annular outer graft 219 along the longitudinal central axial line direction of the first tubular body 21, and less than or equal to ⅔ of the distance between the wave crests and the wave troughs of the wave loop clamped by the annular outer graft 219 along the longitudinal central axial line direction of the first tubular body 21 to ensure that the wave loop may not be separated from the graft and the wave crests and the wave troughs of the wave loop are exposed outside.

It can be understood that in other embodiments, the wave crests on the lesser curvature side of the first tubular body 21 also may be only exposed to achieve the aim of the present application.

Eleventh Embodiment

Figure 31:
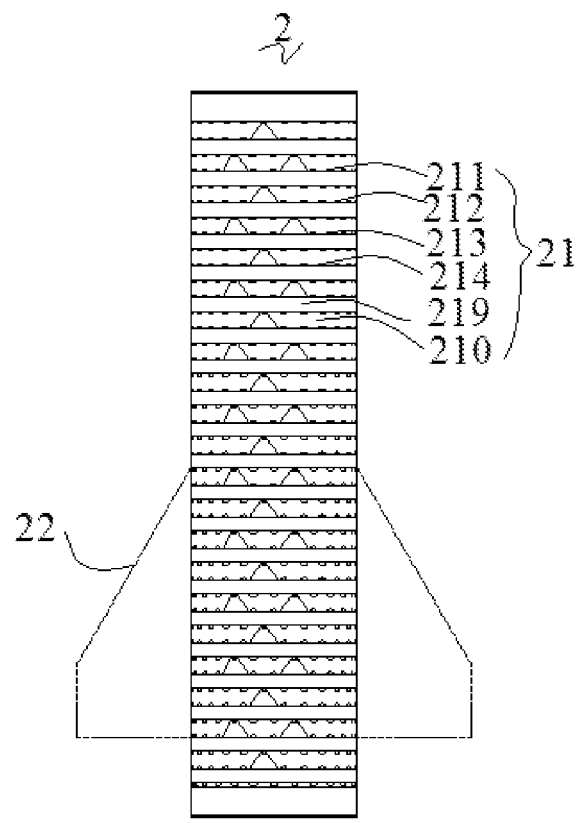
FIG. 31 is a schematic diagram of a luminal stent graft provided by an eleventh embodiment of the present application.

With reference to FIG. 31, a luminal stent graft 2 according to the eleventh embodiment of the present application is approximately similar to the luminal stent graft 2 of the first embodiment of the present application, and includes a first tubular body 21 and a second tubular body 22. The second tubular body 22 is sleeved outside the first tubular body 21, and covers at least one portion of the first tubular body 21; and one end of the second tubular body 22 is sealingly connected with the peripheral surface of the first tubular body 21. The difference between the luminal stent graft 2 of this embodiment and the luminal stent graft 2 of the first embodiment is as follows: the first tubular body 21 of the eleventh embodiment includes barrel-shaped inner grafts 210, a first wave loop group 211, a second wave loop group 212, a third wave loop group 213, a fourth wave loop group 214 and annular outer grafts 219 arranged on the wave loop groups, wherein the second wave loop group 212 is located between the first wave loop group 211 and the third wave loop group 213; the third wave loop group 213 is located between the second wave loop group 212 and the fourth wave loop group 214; and the four wave loop groups are connected through square connecting rings 215, that is to say, the first wave loop group 211, the second wave loop group 212, the third wave loop group 213 and the fourth wave loop group 214 are arrayed in sequence along the longitudinal central axis direction of the first tubular body 21. The annular outer grafts 219 and the barrel-shaped inner grafts 210 may be PET films or PTFE films, and may clamp the wave loops of the first tubular body 21 in a suturing or hot melting way. It can be understood that the first wave loop group 211, the second wave loop group 212, the third wave loop group 213 and the fourth wave loop group 214 form one portion of a bare stent of the first tubular body 21.

Figure 32:
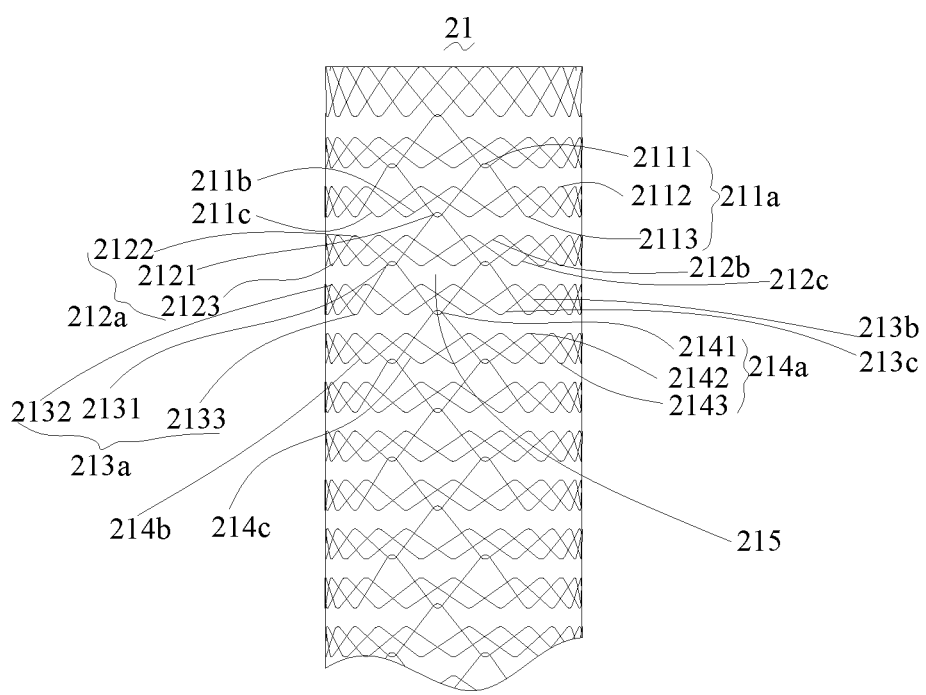
FIG. 32 is a schematic diagram of multiple wave loop groups, which are not covered by the annular outer grafts, of a first tube cavity of the luminal stent graft in FIG. 31.

With reference to FIG. 32 together, the first wave loop group 211 includes a first wave loop 211*a*, a second wave loop 211*b* and a third wave loop 211*c* which are connected. The first wave loop 211*a* has two adjacent relatively high wave crests 2111, multiple relatively low wave crests 2112 and multiple wave troughs 2113; the multiple relatively low wave crests 2112 are parallel and level to one another in the longitudinal central axis direction of the first tubular body 21; the multiple wave troughs 2113 are parallel and level to one another in the longitudinal central axis direction of the first tubular body 21; and the multiple relatively low wave crests 2112 are located between the multiple relatively high wave crests 2111 and the multiple wave troughs 2113.

Multiple wave crests of the second wave loop 211*b*, multiple wave crests of the third wave loop 211*c* and the multiple relatively low wave crests 2112 are parallel and level in the longitudinal central axis direction of the first tubular body 21. Multiple wave troughs of the second wave loop 211*b*, multiple wave troughs of the third wave loop 211*c* and the multiple wave troughs 2113 are parallel and level in the longitudinal central axis direction of the first tubular body 21.

The second wave loop group 212 includes a first wave loop 212*a*, a second wave loop 212*b* and a third wave loop 212*c* which are connected. The first wave loop 212*a* has one relatively high wave crest 2121, multiple relatively low wave crests 2122 and multiple wave troughs 2123; the multiple relatively low wave crests 2122 are parallel and level to one another in the longitudinal central axis direction of the first tubular body 21; the multiple wave troughs 2123 are parallel and level to one another in the longitudinal central axis direction of the first tubular body 21; and the multiple relatively low wave crests 2122 are located between the relatively high wave crest 2121 and the multiple wave troughs 2123. The relatively high wave crest 2121 is hooked and wound with the wave troughs 2113 between the two adjacent relatively high wave crests 2111 of the first wave loop 211*a* to form a whole to connect the first wave loop 211*a* with the first wave loop 212*a*, namely to connect the first wave loop group 211 with the second wave loop group 212. Multiple wave crests of the second wave loop 212*b*, multiple wave crests of the third wave loop 212*c* and the multiple relatively low wave crests 2122 are parallel and level in the longitudinal central axis direction of the first tubular body 21. Multiple wave troughs of the second wave loop 212*b*, multiple wave troughs of the third wave loop 212*c* and the multiple wave troughs 2123 are parallel and level in the longitudinal central axis direction of the first tubular body 21.

The third wave loop group 213 includes a first wave loop 213*a*, a second wave loop 213*b* and a third wave loop 213*c*, which are connected. The first wave loop 213*a* has two adjacent relatively high wave crests 2131, multiple relatively low wave crests 2132 and multiple wave troughs 2133; the multiple relatively low wave crests 2132 are parallel and level to one another in the longitudinal central axis direction of the first tubular body 21; the multiple wave troughs 2133 are parallel and level to one another in the longitudinal central axis direction of the first tubular body 21; and the multiple relatively low wave crests 2132 are located between the multiple relatively high wave crests 2131 and the multiple wave troughs 2133. In the two relatively high wave crests 2131 of the first wave loop 213*a*, the wave crest 2131 on the left side is hooked and wound with the wave trough 2113 on the left side, which is closest to the relatively high wave crest 2121 of the first wave loop 212*a*, and the wave crest 2131 on the right side is hooked and wound with the wave trough 2113 on the right side, which is closest to the relatively high wave crest 2121 of the first wave loop 212*a* to connect the first wave loop 212*a* with the first wave loop 213*a*, namely to connect the second wave loop group 212 with the third wave loop group 213. Multiple wave crests of the second wave loop 213*b*, multiple wave crests of the third wave loop 213*c* and the multiple relatively low wave crests 2132 are parallel and level in the longitudinal central axis direction of the first tubular body 21. Multiple wave troughs of the second wave loop 213*b*, multiple wave troughs of the third wave loop 213*c* and the multiple wave troughs 2133 are parallel and level in the longitudinal central axis direction of the first tubular body 21.

The fourth wave loop group 214 includes a first wave loop 214*a*, a second wave loop 214*b* and a third wave loop 214*c*, which are connected. The first wave loop 214*a* has one relatively high wave crest 2141, multiple relatively low wave crests 2142 and multiple wave troughs 2143; the multiple relatively low wave crests 2142 are parallel and level to one another in the longitudinal central axis direction of the first tubular body 21; the multiple wave troughs 2143 are parallel and level to one another in the longitudinal central axis direction of the first tubular body 21; and the multiple relatively low wave crests 2142 are located between the relatively high wave crest 2141 and the multiple wave troughs 2143. The relatively high wave crest 2141 is hooked and wound with the wave troughs 2133 between the two adjacent relatively high wave crests 2131 of the third wave loop 213*a* to form a whole to connect the third wave loop 213*a* with the fourth wave loop 212*a*, namely to connect the first wave loop group 211 with the second wave loop group 212. Multiple wave crests of the second wave loop 214*b*, multiple wave crests of the third wave loop 214*c* and the multiple relatively low wave crests 2142 are parallel and level in the longitudinal central axis direction of the first tubular body 21. The longitudinal central axis directions of the first tubular body 21, multiple wave troughs of the second wave loop 214*b*, multiple wave troughs of the third wave loop 214*c* and the multiple wave troughs 2143 are parallel and level.

Therefore, the first wave loop group 211, the second wave loop group 212, the third wave loop group 213, and the fourth wave loop group 214 are connected into a whole through the square connecting rings 215.

It can be understood that in each wave loop group, the second wave loop and/or the third wave loop may be omitted as long as each wave loop group has the first wave loop such that the four wave loop groups may be connected through the square connecting rings. It also can be understood that in the four wave loop groups, or in one, two or three wave loop groups, the second wave loop and/or the third wave loop may be omitted as long as each wave loop group has the first wave loop such that the four first wave loops may be connected through the square connecting rings. It also can be understood that the first wave loop group 211 also may not include the first wave loop and/or the second wave loop, and at the moment, the wave troughs of the third wave loop also may be hooked and wound with the relatively high wave crest of the second wave loop group to connect the first wave loop group with the second wave loop group.

Each annular outer graft 219 is also arranged on each wave loop group, and is located between the wave crests and the wave troughs of the wave loop group clamped by it, and the wave crests and the wave troughs of the wave loop group are all exposed outside.

As the wave crests and the wave troughs of each wave loop group are exposed outside (that is to say, the wave crests and the wave troughs of each wave loop group are not wrapped by the annular outer graft 219 and the barrel-shaped inner graft 210), the wave crests and the wave troughs of each wave loop group may be separated from the annular outer graft 219 and the barrel-shaped inner graft 210 (that is to say, the wave crests and the wave troughs of each wave loop group may be all up-warped relative to the annular outer graft 219 and the barrel-shaped inner graft 210); therefore, when the first tubular body 21 is bent, on the lesser curvature side, in two adjacent wave loop groups, one wave loop group may be overlapped with the other wave loop group, thereby improving the softness of the first tubular body 21. In addition, it is precisely because the wave crests and the wave troughs of the wave loop groups are exposed outside that it is difficult for the wave crests or the wave troughs of the wave loop groups to puncture the barrel-shaped inner grafts in the bending process, thus prolonging the service life of the first tubular body 21.

in this embodiment, the wave loops at two ends of the first tubular body 21 are all covered by the annular outer grafts 219, that is to say, the wave loops at the two ends are all covered by the annular outer grafts 219 and the barrel-shaped inner grafts 210, so that the softness of the first tubular body 21 may be better improved. In addition, in this embodiment, the wave loop groups may be connected into a whole through the annular outer grafts 219 and the barrel-shaped inner grafts 210, and also may be connected into a whole through the square connecting rings 215, so that the stability of the first tubular body 21 is improved, the softness of the first tubular body 21 is also increased, and the service life of the first tubular body 21 is prolonged.

It can be understood that in other embodiments, the bare stent of the first tubular body also may include a first wave loop group, a second wave loop group, a third wave loop group and a fourth wave loop group which are connected through square connecting rings.

Above all, the luminal stent graft according to each embodiment of the present application includes the first tubular body and the second tubular body which covers at least one part of the radial supporting section of the first tubular body; after the luminal stent graft is implanted, the semi-closed clearance may be formed between the first tubular body and the second tubular body, or the semi-closed clearance may be formed between the second tubular body and the lumen wall; and the blood flowing into the above-mentioned clearances may be used as the filling material to plug the type-I endoleak channel, thus avoiding the blood from flowing into the tumor body or the dissection.

In addition, the first tubular body and the second tubular body both have the radial supportabilities, namely the radial supporting forces, so that after the luminal stent graft is implanted into the lumen, the first tubular body and the second tubular body still may be attached to the lumen wall by their radial supporting forces under the radial compression of the lumen wall; and at the same time, under the impact of the blood flow, the first tubular body and the second tubular body may keep radial supporting shapes to avoid occurrence of the deformation such as wrinkling, introversion and collapse, and particularly to ensure that no deformation occurs on the proximal end face of the luminal stent graft, thereby avoiding blocking the blood flowing into the lumen.

In addition, the second tubular body has relatively high radial deformability when compared with the first tubular body, so that under the radial compression action of the lumen wall, the first tubular body may guarantee no lumen loss and keep unblocked blood flow, and the second tubular body may adapt to the deformations of the lumen wall and the first tubular body when attached to the lumen wall; and formation of the type-I endoleak is prevented through the clearance between the first tubular body and the second tubular body or the clearance between the second tubular body and the lumen wall.

In addition, in the stent system according to the embodiment of the present application, the luminal stent graft according to the embodiments of the present application may cooperate with other conventional luminal stent grafts, or multiple luminal stent grafts according to the embodiments of the present application may cooperate with one another to be implanted into the lumen having the branch blood vessels, thereby isolating the tumor body or the dissection, guaranteeing unblocked blood flow in the branch blood vessels and preventing formation of the type-I endoleak.

The invention claimed is:

1. A luminal stent graft, comprising:
   a first tubular body and a second tubular body, wherein the second tubular body is sleeved outside the first tubular body, and at least one end of the second tubular body is sealingly connected with an outer surface of the first tubular body;
   the first tubular body comprises at least one first radial supporting structure distributed along a circumferential direction of the first tubular body,
   the second tubular body comprises a graft covering at least one portion of the first tubular body, and a second radial supporting structure which is arranged in a maximum radial length region of the graft and surrounds the maximum radial length region, and
   the second radial supporting structure has radial supportability, wherein radial deformability of the second radial supporting structure than that of the first radial supporting structure.

2. The luminal stent graft according to claim 1, wherein, in a naturally unfolded state, at a same position in a radial supporting section, a radial length of the second radial supporting structure is 1.3 times to 3 times the radial length of the first radial supporting structure.

3. The luminal stent graft according to claim 1, wherein, in a naturally unfolded state, a radial length of the second radial supporting structure is more than that of the first radial supporting structure by 2 mm to 30 mm.

4. The luminal stent graft according to claim 1, wherein under the action of a same radial force, a radial length variation of the second radial supporting structure is greater than that of the first radial supporting structure;
   or under the action of a same radial force, a radial length change rate of the second radial supporting structure is greater than that of the first radial supporting structure;
   or in case of the same radial change rate or the same radial variation, a radial external force exerted on the first radial supporting structure is greater than that exerted on the second radial supporting structure.

5. The luminal stent graft according to claim 1, wherein the second radial supporting structure is a waveform ring-like object; and
   in a naturally unfolded state, a maximum width m of any waveform of the waveform ring-like object along a circumferential direction and a perimeter D of the second tubular body at the waveform accord with a condition that m is less than or equal to D/8.

6. The luminal stent graft according to claim 1, wherein the second radial supporting structure is of a meshed structure comprising multiple grids; and
   in the naturally unfolded state, the maximum width m1 of any grid along the circumferential direction and the perimeter D of the second tubular body at the grid accord with a condition that m1 is less than or equal to D/12.

7. The luminal stent graft according to claim 1, wherein in the portion covered by a graft, the first tubular body further comprises a first graft covering the first radial supporting structure.

8. The luminal stent graft according to claim 1, wherein one end of the graft is sealingly connected with the first tubular body, and the other end of the graft is open; and
   the maximum radial length region of the graft is located near to an opening of the open end, or is located at the middle portion of the graft.

9. The luminal stent graft according to claim 1, wherein two ends of the graft are sealingly connected with the first tubular body, and the maximum radial length region of the graft is located at the middle portion of the graft.

10. The luminal stent graft according to claim 1, wherein at least one end of the first tubular body has multiple convex pieces extending in parallel to the longitudinal axis of the first tubular body, and a gap is reserved between two adjacent convex pieces.

11. The luminal stent graft according to claim 1, wherein the first tubular body comprises four wave loops arrayed in sequence along a longitudinal central axis direction of the first tubular body, and the four wave loops are connected through square connecting rings.

12. The luminal stent graft according to claim 1, wherein the first tubular body comprises barrel-shaped inner grafts, wave loops and annular outer grafts;
   the wave loops are arranged between the barrel-shaped inner grafts and the annular outer grafts in a clamping manner; and
   at least part of wave crests and/or wave troughs of the wave loops are exposed outside.

13. The luminal stent graft according to claim 1, wherein a graft is arranged on the first tubular body; and
   a hole penetrating through the graft is formed in a portion, which is near to an end portion of the first tubular body, on the graft or a wave loop, which is close to the end portion of the first tubular body, of the first tubular body is not completely covered by the graft.

* * * * *